(12) United States Patent
Horn et al.

(10) Patent No.: US 11,993,093 B2
(45) Date of Patent: May 28, 2024

(54) HEAT-SENSITIVE RECORDING MATERIAL

(71) Applicant: PAPIERFABRIK AUGUST KOEHLER SE, Oberkirsch (DE)

(72) Inventors: Michael Horn, Offenburg (DE); Kerstin Zieringer, Achern (DE)

(73) Assignee: Papierfabrik August Koehler SE, Oberkirch (DE)

( * ) Notice: Subject to any disclaimer, the term of this patent is extended or adjusted under 35 U.S.C. 154(b) by 350 days.

(21) Appl. No.: 16/319,076

(22) PCT Filed: Jul. 6, 2017

(86) PCT No.: PCT/EP2017/067044
§ 371 (c)(1),
(2) Date: Jan. 18, 2019

(87) PCT Pub. No.: WO2018/015178
PCT Pub. Date: Jan. 25, 2018

(65) Prior Publication Data
US 2021/0331508 A1 Oct. 28, 2021

(30) Foreign Application Priority Data

Jul. 18, 2016 (DE) ..................... 10 2016 113 203.9

(51) Int. Cl.
*B41M 5/333* (2006.01)
*B41M 5/323* (2006.01)
*B41M 5/337* (2006.01)

(52) U.S. Cl.
CPC .......... *B41M 5/3333* (2013.01); *B41M 5/323* (2013.01); *B41M 5/3375* (2013.01)

(58) Field of Classification Search
CPC .. B41M 5/323; B41M 5/3333; B41M 5/3375; C07C 311/60
See application file for complete search history.

(56) References Cited

U.S. PATENT DOCUMENTS

| | | | |
|---|---|---|---|
| 5,972,577 A | 10/1999 | Komatsu et al. | |
| 6,624,117 B1 * | 9/2003 | Heneghan | C07C 311/62 503/216 |
| 7,833,573 B2 | 11/2010 | Boschert et al. | |
| 9,518,011 B2 | 12/2016 | Sakai et al. | |
| 2002/0132179 A1 | 9/2002 | Yamada et al. | |
| 2004/0029056 A1 | 2/2004 | Tsukada | |
| 2009/0082202 A1 * | 3/2009 | Stork | B41M 5/3275 503/217 |

FOREIGN PATENT DOCUMENTS

| | | |
|---|---|---|
| DE | 102004029261 B4 | 5/2006 |
| EP | 0526072 A1 | 3/1993 |
| EP | 0535887 A1 | 4/1993 |
| EP | 0542556 A1 | 5/1993 |
| EP | 0604832 B1 | 7/1994 |
| EP | 0620122 B1 | 7/1994 |
| EP | 0701905 A | 3/1996 |
| EP | 0860738 A1 | 8/1998 |
| EP | 1044824 A2 | 10/2000 |
| JP | 6447757 A | 2/1989 |
| JP | S6447757 A | 2/1989 |
| JP | 10239808 A | 9/1989 |
| JP | 6064335 A | 3/1994 |
| JP | 0858242 A | 3/1996 |
| JP | H08132737 A | 5/1996 |
| JP | 11263067 A | 9/1999 |
| JP | H0986050 A | 10/1999 |
| JP | 20000291458 A | 1/2000 |
| JP | 2000075436 A | 3/2000 |
| JP | 2002055408 A | 2/2002 |
| KR | 1020150065884 A | 6/2015 |
| WO | 200035679 A1 | 6/2000 |
| WO | 20000035679 A1 | 6/2000 |
| WO | 2014080615 A1 | 5/2014 |
| WO | 2015181291 A1 | 3/2015 |

(Continued)

OTHER PUBLICATIONS

Office Action of Korean Application No. 10-2019-7004319, dated Apr. 1, 2020, 25 pages.
F. Briganti et al., European Journal of Medicinal Chemistry, 1997, 32(11), p. 901-910, "Sulfonylamido derivatives of aminoglutethimide and their copper (II) complexes: a novel class of antifungal compounds".
A. Mastrolorenzo et al., Journal of Enzyme Inhibition, 2000, 15(6), p. 517-531, "Antifungal activity of AG(I) and ZN(II) complexes of aminobenzolamide (5-sulfanilylamido-1,3,4-thiadiazole-2-sulfonamide) derivatives".
A. Mastrolorenzo et al., European Journal of Medicinal Chemistry, 2000, 11(2), p. 99-107, "Antifungal activity of silver and zinc complexes of sulfadrug derivatives incorporating arylsulfonylureido moieties".

(Continued)

*Primary Examiner* — Gerard Higgins
(74) *Attorney, Agent, or Firm* — Lippes Mathias LLP

(57) ABSTRACT

The invention relates to a color developer of the formula (I), wherein m and n independently of one another are ≥1, $Ar^1$ is an unsubstituted or substituted (hetero) aromatic radical, $Ar^2$ is an unsubstituted or substituted phenyl radical, and Y is at least one (m+n)-times substituted benzene or naphthalene group, and to a heat-sensitive recording material, comprising a supporting substrate and a heat-sensitive color-forming layer containing at least one color former and at least one phenol-free color developer, wherein the at least one color developer is the compound of the formula (I). The invention further relates to a method for producing said heat-sensitive recording material.

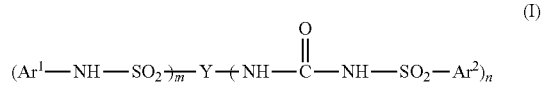

(I)

10 Claims, No Drawings

(56) References Cited

FOREIGN PATENT DOCUMENTS

WO          2015181291 A1    12/2015

OTHER PUBLICATIONS

C.T. Supuran et al., European Journal of Medicinal Chemistry, 1998, 33(10), p. 821-830, "The antifungal activity of sulfonylamido derivatives of 2-aminophenoxathiin and related compounds".
C.T. Supuran et al., Journal of Enzyme Inhibition, 1998, 13(4), p. 291-310, "Sulfonylamindo derivatives of 2-aminophenoxathiin-10, 10-dioxide and related compounds possess antifungal action due to the possible inhibition of lanosterol-14-a-demethylase".
PCT/EP2017/067044, International Search Report, mailed Sep. 13, 2017, 8 pages.
Office Action for Japanese Application No. 2019-502188, dated Feb. 25, 2022, 3 pages.
Office Action for Chinese Application No. 201780044595.2, dated Aug. 13, 2021, 3 pages.
Office Action for Japanese Application 2019-502188, dated Apr. 26, 2021, 8 pages.
Claudiu T. Supuran et al., "The antifungal activity of sulfonylamido derivative of 2-aminophenoxathiin and related compounds", Eur. J. Med. Chem. 33 (1998), pp. 821-830.
Antonio Mastrolorenzo et al., "Antifungal Activity of AG(I) and ZN(II) Complexes of Aminobenzolamide (5-Sulfanilylamido-1,3,4-Thiadiazole-2Sulfonamide) Derivatives", J. Enzyme Inhibition, 2000, vol. 15, pp. 517-531.
Antonio Mastrolorenzo et al., "Antifungal activity of silver and zinc complexes of sulfadrug derivatives incorporating arylsulfonylureido moieties", European Journal of Pharmaceutical Sciences 11 (2000), p. 99-107.
F. Briganti et al., "Sulfonylamido derivatives of aminoglutethimide and their copper (II) complexes: a novel class of antifungal compounds", European J. Med. Chem., (1997) 32, p. 901-910.

* cited by examiner

HEAT-SENSITIVE RECORDING MATERIAL

The invention relates to a color developer, a heat-sensitive recording material, comprising a supporting substrate as well as heat-sensitive color-forming layer containing at least one color former and at least this color developer, a method for its production and the use of the phenol-free color developer contained in the heat-sensitive recording material.

Heat-sensitive recording materials for use in direct thermal printing and having a heat-sensitive color-forming layer (thermoresponse layer) superimposed on a supporting substrate have long been known. In the heat-sensitive color-forming layer there are usually a color former and a color developer, which react with one another in response to heat and thus lead to color development. Low-priced phenolic color developers, e.g. bisphenol A and bisphenol S, with which may be obtained heat-sensitive recording materials having an acceptable performance profile for numerous uses, are widespread. Also known are heat-sensitive recording materials that contain non-phenolic color developer in the heat-sensitive color-forming layer. These were developed to improve the durability of the typeface, in particular when the printed heat-sensitive recording material is stored for a longer time or comes into contact with hydrophobic substances, such as plasticizer-containing materials or oils. In light of the public discussions regarding the toxic potential of (bis)phenolic chemicals, the interest in non-phenolic color developers has greatly increased. The goal here was to avoid the disadvantages of phenolic color developers; however, the technical performance properties that may be achieved with phenolic color developers should at least be maintained, but preferably be improved.

Despite the great chemical diversity of these substances, common structural features can be recognized in the prior art of non-phenolic color developers.

Thus, a 1,3-disubstituted ureide structure (Y—NH—CO—NH—Z) is a common feature of numerous non-phenolic color developers. Through the appropriate choice of groups Y and Z, the functional properties essential to suitability as a color developer, in particular the acidity and hydrogen bond donor properties, may be modulated.

Widespread are color developers with sulfonylurea structures —$SO_2$—NH—CO—NH— because these are relatively easy to produce and the heat-sensitive recording materials produced with them have relatively good application-specific properties.

EP 0 526 072 A1 discloses color developers belonging to the group of aromatic sulfonyl(thio)urea compounds of the formula

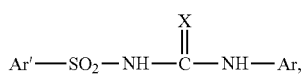

wherein X is O or S.

With these can be obtained heat-sensitive recording materials characterized by improved image durability. Furthermore, the heat-sensitive recording materials based on these color developers have a thermic pressure sensitivity that can be used with good surface whiteness so that it is comparatively easy, with the corresponding design of the recipe for the heat-sensitive color-forming layer, to create high print densities using commercially available thermal printers.

WO 0 035 679 A1 discloses aromatic and heteroaromatic sulfonyl(thio)urea compounds (X=S or O) and/or sulfaguanidine (X=NH) of the above formula, wherein Ar is joined to further aromatic groups by a bivalent linker group. A non-phenolic color developer belonging to this group and that is widespread in practice, 4-methyl-N-[[[3-[[(4-methylphenyl)sulfonyl]oxy]phenyl]amino]carbonyl]-benzene sulfonamide (trade name Pergafast 201®, BASF), is characterized by a balance in the application-specific properties of the heat-sensitive recording materials produced with this color developer. In particular, these possess good dynamic responsiveness and high durability of the printout vis-à-vis hydrophobic substances.

A great deal has also been written about a bivalent or multivalent linker group A bonded sulfonylurea units, e.g. bis-sulfonylurea compounds, of the formula

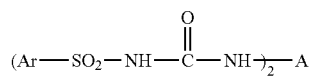

as a color developer (cf. EP 0 535 887 A1, EP 0 542 556 A1, EP 0 604 832 B1, EP 0 620 122 A1 and EP 1 044 824 A2).

In practice, N,N'[methylenebis(4,1-phenyleniminocarbonyl)]bis[4-methyl-benzene sulfonamide] (B-TUM) in particular has become accepted.

The subject-matter of JP H 0 664 335 is the combination of a sulfonylurea structure with an N-sulfonyl(thiol)urethane group of the formula

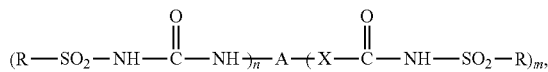

wherein R is an aromatic radical, A an (m+n)valent organic linker group and X=O or S.

For the heat-sensitive recording materials produced with these color developers, increased durability of the typeface vis-à-vis hydrophobic agents is described. However, the synthetic access to these color developers is problematic when chemically homogeneous substances are desired.

JP H 0 958 242 combines sulfonylurea substructures with primary sulfone amide groups to obtain developers of the formula

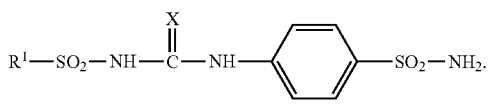

JP H 11-263067 discloses color developers made up of (thio)urea and sulfonyl(thio)urea substructures bonded via an aromatic linker unit of the formula

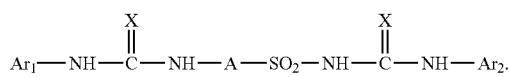

The heat-sensitive recording materials with non-phenolic color developers and based on sulfonylurea chemistry have in common that they demonstrate high performance in many application-relevant properties, but disclose weaknesses in others.

Thus, high durability of the typeface vis-à-vis hydrophobic substances often accompanies a moderate responsiveness (dynamic sensitivity) in the thermal printer, for example, which may be effectively improved through the use of large quantities of partially very special melting aids (special thermic solvents, special sensitizers).

On the other hand, relatively slightly high dynamic sensitivity values are achieved with certain non-phenolic color developers, wherein however the durability of the typeface is moderate. Through the use of anti-aging agents (stabilizers), this fault may be eliminated, though at the cost of a complex and expensive recipe for the recording layer.

The effect of the present invention is thus to eliminate the aforementioned disadvantages of the prior art. In particular, the effect of the present invention is to create a color developer and a heat-sensitive recording material containing this, which has a balanced application-specific property profile and achieves at least the performance of the heat-sensitive recording materials based on known non-phenolic color developers without depending on special recipe components in the heat-sensitive functional layer, such as anti-aging agents, or special melting aids with limited availability and/or high prices. A primary effect of the invention is to create color developers that make the formation of highly stable color complexes possible and thus allow for considerably higher durability of the typeface of the heat-sensitive recording material in comparison with the prior art.

According to the invention, this effect is achieved through the use of a compound according to claim 1 in a heat-sensitive recording material according to claim 9.

The compound according to claim 1 has the formula (I),

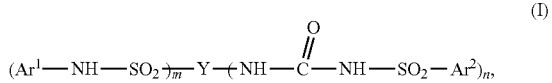

(I)

wherein m and n independently of one another are ≥1, $Ar^1$ is an unsubstituted or substituted (hetero) aromatic radical, $Ar^2$ is an unsubstituted or substituted phenyl radical and Y is at least one (m+n)-times substituted benzene or naphthalene group.

Preferably, m is 1 or 2, particularly preferred 1.

Preferably, n is 1 or 2, particularly preferred 1.

Preferably, m is 1 and n is 1, m is 1 and n is 2 or m is 2 and n is 2.

Preferably, $Ar^1$ is an unsubstituted phenyl, an unsubstituted 1-napthyl radical, an unsubstituted 2-naphtyl radical, a monosubstituted phenyl radical, a monosubstituted 1-napthyl radical or a monosubstituted 2-naphtyl radical. It is particularly preferred that $Ar^1$ be an unsubstituted phenyl radical or a monosubstituted phenyl radical. It is very particularly preferred that $Ar^1$ be an unsubstituted phenyl radical or a 4-alkoxycarbonylphenyl radical. The former is easy to produce; the latter provides particularly good results.

The substituted (hetero) aromatic radical, in particular the substituted phenyl radical, is preferably substituted with a $C_1$-$C_5$-alkyl radical, an alkenyl radical, an aklinyl radical, a benzyl radical, an RO radical, a halogen radical, an ROC radical, an $RO_2C$ radical, a CN radical, an $NO_2$ radical, an R—$SO_2O$ radical, an RO—$SO_2$ radical, an R—NH—$SO_2$ radical, an R—$SO_2$NH radical, an R—NH—CO—NH radical, an R—$SO_2$—NH—CO—NH radical, an R—NH—CO—NH—$SO_2$ radical or an R—CO—NH radical, wherein R is a $C_1$-$C_5$-alkyl radical, an alkenyl radical, an alkinyl radical, a phenyl radical, a tolyl radical or a benzyl radical, preferably a phenyl or p-tolyl radical. Preferable substitutions are $C_1$-$C_5$-alkyl, RO, halogen, $RO_2C$, R—$SO_2O$, R—NH—CO—NH and R—$SO_2$—NH—CO—NH radicals.

$Ar^1$ may also be a polysubstituted (hetero) aromatic radical.

$Ar^2$ is preferably an unsubstituted phenyl or a monosubstituted phenyl radical. The monosubstituted phenyl radical is preferably substituted with a $C_1$-$C_4$-alkyl radical, particularly preferably with a methyl radical and very particularly preferably with a 4-methyl radical or with a halogen radical.

Y is particularly preferably an (m+n)times substituted benzene group. The sum of (m+n) is particularly preferably 2, 3 or 4, particularly 2, i.e. Y is a phenylene group since compounds of this type can be produced cheaply.

In a preferred embodiment, $Ar^1$ is an unsubstituted phenyl radical or a monosubstituted phenyl radical, $Ar^2$ is an unsubstituted phenyl radical or a monosubstituted phenyl radical and Y is an (m+n)times substituted benzene group.

Particularly preferred compounds of the formula (I) are presented in the following Table 1.

TABLE 1

Preferred compounds of the formula (I) with the provided meanings for the Y group, the $Ar^1$ radical, the $Ar^2$ radical, m and n (R = as previously stated)

| Y | $Ar^1$ | $Ar^2$ | m | n |
|---|---|---|---|---|
| Phenylene | Phenyl | Phenyl | 1 | 1 |
| Phenylene | $C_1$-$C_5$-alkyl substituted phenyl | Phenyl | 1 | 1 |
| Phenylene | RO substituted phenyl | Phenyl | 1 | 1 |
| Phenylene | $RO_2C$ substituted phenyl | Phenyl | 1 | 1 |
| Phenylene | Halogen substituted phenyl | Phenyl | 1 | 1 |
| Phenylene | R—NH—CO—NH substituted phenyl | Phenyl | 1 | 1 |
| Phenylene | Phenyl | $C_1$-$C_4$-alkyl substituted phenyl | 1 | 1 |
| Phenylene | $C_1$-$C_5$-alkyl substituted phenyl | $C_1$-$C_4$-alkyl substituted phenyl | 1 | 1 |
| Phenylene | RO substituted phenyl | $C_1$-$C_4$-alkyl substituted phenyl | 1 | 1 |
| Phenylene | $RO_2C$ substituted phenyl | $C_1$-$C_4$-alkyl substituted phenyl | 1 | 1 |
| Phenylene | Halogen substituted phenyl | $C_1$-$C_4$-alkyl substituted phenyl | 1 | 1 |
| Phenylene | R—NH—CO—NH substituted phenyl | $C_1$-$C_4$-alkyl substituted phenyl | 1 | 1 |

TABLE 1-continued

Preferred compounds of the formula (I) with the provided meanings for the Y group, the Ar¹ radical, the Ar² radical, m and n (R = as previously stated)

| Y | Ar¹ | Ar² | m | n |
|---|---|---|---|---|
| Trisubstituted benzene | Phenylene | Phenyl | 1 | 2 |
| Trisubstituted benzene | Phenylene | $C_1$-$C_4$-alkyl substituted phenyl | 1 | 2 |
| Tetrasubstituted benzene | Phenylene | Phenyl | 2 | 2 |
| Tetrasubstituted benzene | Phenylene | $C_1$-$C_4$-alkyl substituted phenyl | 2 | 2 |
| Tetrasubstituted benzene | $RO_2$C-substituted phenyl | $C_1$-$C_4$-alkyl substituted phenyl | 2 | 2 |

The compound of the formula (I) according to the invention may be produced using known methods. The following reaction schema illustrates a possible synthesis pathway for the compound of the formula (I) according to the invention using the example of the compounds I-XXXII (cf. Table 2).

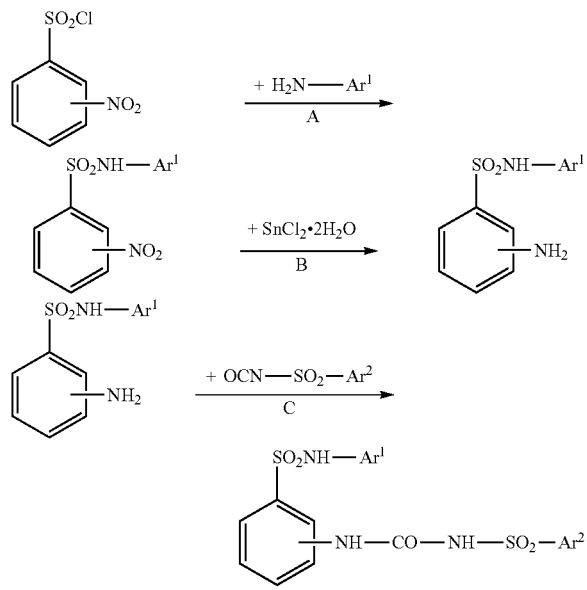

The compounds XXXIII-XXXIV (cf. Table 2) falling under the compound of the formula (I) according to the invention may be converted into the bis-amino benzene bis-sulfone anilide according to the following reaction schema based on the corresponding bis-aminosulfonyl chloride (G. Barnikow, K. Krüger, G. Hilgetag, Z. Chem., 6, (7), 262 (1966)) and then further processed into the final product.

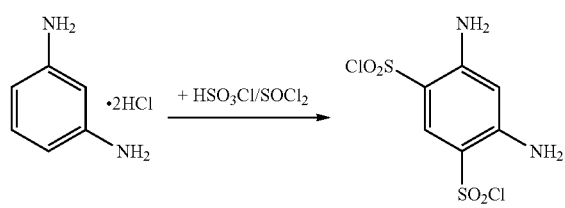 [SMILES: Nc1cccc(N)c1 ; Nc1cc(N)c(S(=O)(=O)Cl)cc1S(=O)(=O)Cl]

The preferred embodiments explained in connection with the compound of the formula (I) also apply for the method for its production.

As already mentioned above, the present compound also relates to a heat-sensitive recording material comprising a supporting substrate as well as a heat-sensitive color-forming layer containing at least one color former and one phenol-free color developer, wherein the at least one phenol-free color developer is the compound of the previously described formula (I).

The compound of the formula (I) is preferably present in a quantity of approximately 3 to approximately 35 weight percent, particularly preferably in a quantity of approximately 10 to approximately 25 weight percent, referring to the total solid content of the heat-sensitive layer.

The choice of the supporting substrate is not critical. However, it is preferred that paper, synthetic paper and/or a plastics material foil be used as the supporting substrate.

Where applicable, between the supporting substrate and the heat-sensitive layer is at least one further interlayer. In addition, at least one protective layer and/or at least one layer contributing to the printability or the barrier properties may be included in the heat-sensitive recording material according to the invention, wherein these layers may be applied to the front or reverse side of the substrate.

With regard to the choice of the color former, the present invention also is not subject to any essential limitations. However, the color former is preferably a dye of the triphenylmethane, fluoran, azaphthalide and/or fluoren type. A very particularly preferred color former is a dye of the fluoran type, as it makes it possible to create a recording material with an attractive price/performance ratio thanks to the availability and the balanced application-specific properties.

Particularly preferred dyes of the fluoran type are:
3-diethylamino-6-methyl-7-anilinofluoran,
3-(N-ethyl-N-p-toludinamine)-6-methyl-7-anilinofluoran,
3-(N-ethyl-N-isoamylamine)-6-methyl-7-anilinofluoran,
3-diethylamino-6-methyl-7-(o,p-dimethylaniline)fluoran,
3-pyrrolidino-6-methyl-7-anilinofluoran,
3-(cyclohexyl-N-methylamine)-6-methyl-7-anilinofluoran,
3-diethylamin-7-(m-trifluoromethylaniline)fluoran,
3-N-n-dibutylamin-6-methyl-7-anilinofluoran,
3-diethylamino-6-methyl-7-(m-methylaniline)fluoran,
3-N-n-dibutylamin-7-(o-chloroaniline)fluoran,
3-(N-ethyl-N-tetrahydrofurfurylamine)-6-methyl-7-anilinofluoran,
3-(N-methyl-N-propylamine)-6-methyl-7-anilinofluoran,
3-(N-ethyl-N-ethoxypropylamine)-6-methyl-7-anilinofluoran,
3-(N-ethyl-N-isobutylamine)-6-methyl-7-anilinofluoran and/or
3-dipentylamine-6-methyl-7-anilinfluoran.

The color formers may be used as individual substances and as any mixtures of two or more color formers on condition that desired application-specific properties of the recording material do not suffer therefrom.

The color formers are preferably present in a quantity of approximately 5 to approximately 30 weight percent, particularly preferably in a quantity of approximately 8 to approximately 20 weight percent, referring to the total solid content of the heat-sensitive layer.

To control special application-specific properties, it may be advantageous if at least two compounds falling under the formula (I) are present as color developers in the heat-sensitive layer. Likewise, one or more additional (bis)phenolic or non-phenolic color developers may be present in addition to compounds of the formula (I) in the heat-sensitive color-forming layer.

In addition to the at least one color former and the at least one color developer, in the heat-sensitive color-forming layer may be present one or more sensitizers (also known as thermic solvents), which has the advantage that the thermic pressure sensitivity may be more easily controlled.

Generally considered as sensitizers are advantageously crystalline substances whose melting point is between approximately 90 and approximately 150° C. and which dissolve the color-forming components (color formers and color developers) in the melted state without interfering with the formation of the color complex.

The sensitizer is preferably a fatty acid amide, such as stearamide, behenamide or palmitamide, an ethylene-bis-fatty acid amide, such as N,N'-ethylene-bis-stearine acid amide or N,N'-ethylene-bis-oleic acid amide, a fatty acid alkanolamide, such as N-(hydroxymethyl)stearamide, N-hydroxymethylpalmitamide or hydroxyethylstearamide, a wax, such as polyethylene wax or montan wax, a carboxylic acid ester, such as dimethylterephthalate, dibenzylterephthalate, benzyl-p-benzyloxybenzoate, di-(p-methylbenzyl)oxylate, di-(p-chlorbenzyl)oxalate or di-(p-benzyl)oxalate, an aromatic ether, such as 1,2-diphenoxy-ethane, 1,2-di-(3-methylphenoxy)ethane, 2-benzyloxynaphthaline or 1,4-di-ethoxynaphthaline, an aromatic sulfone, such as diphenyl sulfone, and/or an aromatic sulfone amide, such as benzene sulfone anilide or N-benzyl-p-toluol sulfone amide.

The sensitizer is preferably present in a quantity of approximately 10 to approximately 40 weight percent, particularly preferably in a quantity of approximately 15 to approximately 25 weight percent, referring to the total solid content of the heat-sensitive layer.

In a further preferred embodiment, in addition to the color former, the phenol-free color developer and the sensitizer is optionally present at least one stabilizer (anti-aging agent) in the heat-sensitive color-forming layer.

The stabilizer is preferably sterically hindered phenols, particularly preferably 1,1,3-tris-(2-methyl-4-hydroxy-5-cyclohexyl-phenyl)-butane, 1,1,3-tris-(2-methyl-4-hydroxy-5-tert-butylphenyl)-butane, 1,1-bis-(2-methyl-4-hydroxy-5-tert-butyl-phenyl)butane.

Also utilizable as stabilizers in the recording material according to the invention are urea-urethane compounds of the general formula (II), commercial product UU (urea-urethane) or ethers derived from 4,4'-dihydroxydiphenyl sulfone, such as 4-benzyloxy-4'-(2-methylglycidyloxy)-diphenyl sulfone (trade name NTZ-95®, Nippon Soda Co. Ltd.) or oligomer ethers of the general formula (III) (trade name D90®).

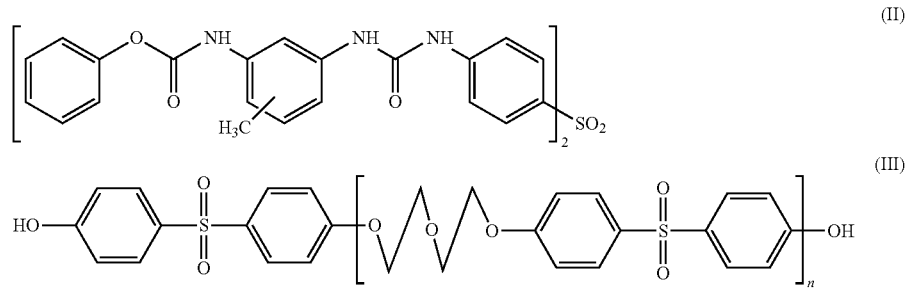

Particularly preferred are the urea-urethane compounds of the general formula (II).

The stabilizer is preferably present in a quantity of 0.2 to 0.5 weight percent, referring to the at least one phenol-free color developer of the compound of the formula (I).

In a further preferred embodiment is present in the heat-sensitive color-forming layer at least one binding agent. This is preferably water-soluble starches, starch derivatives, starch-based biolatices of the EcoSphere® type, methyl cellulose, hydroxyethyl cellulose, carboxymethyl celluloses, partially or fully saponified polyvinyl alcohols, chemically modified polyvinyl alcohols or styrene maleic acid anhydride copolymers, styrene-butadiene copolymers, acrylamide-(meth)-acrylate-copolymers, acrylamide-acrylate-methacrylate-terpolymers, polyacrylates, poly(meth)-acryl acid esters, acrylate-butadiene-copolymers, polyvinyl acetates and/or acrylonitrile-butadiene-copolymers.

In a further preferred embodiment is present at least one release agent (anti-adhesive agent) or lubricant in the heat-sensitive color-forming layer. These agents are preferably fatty acid metal salts, e.g. zinc stearate or calcium stearate, or also behenic salt, synthetic waxes, e.g. in the form of fatty acid amides, e.g. stearic acid amide and behenic acid amide, fatty acid alkanolamides, e.g. stearic acid methylolamide, paraffin waxes with various melting points, ester waxes with various molecular weights, ethylene waxes, propylene waxes with various hardnesses and/or natural waxes, e.g. carnauba wax or montan wax.

The release agent is preferably present in a quantity of approximately 1 to approximately 10 weight percent, particularly preferably in a quantity of approximately 3 to approximately 6 weight percent, referring to the total solid content of the heat-sensitive layer.

In a further preferred embodiment, the heat-sensitive color-forming layer contains pigments. Their use has, among others, the advantage that they can fuse the chemical melts developing during the thermic printing process to their surface. The surface whiteness and opacity of the heat-sensitive color-forming layer and its printability with conventional printing colors can also be controlled via pigments. Finally, pigments have an "extender function," e.g. for the relatively expensive coloring functional chemicals.

Particularly well-suited pigments are inorganic pigments, with both synthetic and natural origins, preferably clays, precipitated or natural calcium carbonates, aluminum oxides, aluminum hydroxides, silica, precipitated and pyrogenous silica (e.g. nanoscale qualities like Aerodisp® types), diatomaceous earths, magnesium carbonates, talc, but also organic pigments, such as hollow pigments with a styrene/acrylate-copolymer wall or urea/formaldehyde-condensation polymers. These may be used alone or in any combination.

The pigments are preferably present in a quantity of approximately 20 to approximately 50 weight percent, particularly preferably in a quantity of approximately 30 to approximately 40 weight percent, referring to the total solid content of the heat-sensitive layer.

To control the surface whiteness of the heat-sensitive recording material according to the invention, optical brighteners may be incorporated into the heat-sensitive color-forming layer. These are preferably stilbenes.

To improve certain coating properties, in individual cases it is preferable to add further components, particularly rheology additives, e.g. thickeners and/or tensides, to the necessary components of the heat-sensitive recording material according to the invention.

As mentioned above, the heat-sensitive color-forming layer may therefore preferably contain usual additives, e.g. sensitizers, stabilizers, binding agents, release agents, pigments and/or brighteners.

The surface application weight of the (dry) heat-sensitive layer is preferably approximately 1 to approximately 10 $g/m^2$, preferably approximately 3 to approximately 6 $g/m^2$.

In a particularly preferred embodiment, the heat-sensitive recording material is one according to claim 10, wherein a fluoran-type dye is used as a color former and a sensitizer, chosen from the group consisting of fatty acid amides, aromatic sulfones and/or aromatic ethers, is also present. In this preferred embodiment, it is also advantageous for approximately 1.5 to approximately 4 weight percent of the phenol-free color developer according to claim 1, referring to the color former, to be present.

The preferred embodiments described in connection with the compound of the formula (I) are also valid for the heat-sensitive recording material according to the invention.

The heat-sensitive recording material according to the invention can be created using known production methods.

However, it is preferred that the heat-sensitive recording material according to the invention be created with a method wherein an aqueous suspension containing the raw materials of the heat-sensitive color-forming layer is applied to a supporting substrate and dried, wherein the aqueous application suspension has a solid content of approximately 20 to approximately 75 weight percent, preferably of approximately 30 to approximately 50 weight percent, and which is applied with the curtain-coating method with a coater operating speed of at least approximately 400 m/min and dried.

This method is particularly advantageous from an economic standpoint.

If the solid content value falls below approximately 20 weight percent, the economic viability decreases because a large quantity of water must be removed from the coat in a short time using gentle drying, which has negative effects on the coating speed. If, on the other hand, the value of 75 weight percent is exceeded, this only leads to an increased technical effort to guarantee the stability of the coating color curtain during the layering process.

As mentioned above, it is advantageous to produce the heat-sensitive recording material according to the invention using a method wherein the aqueous application suspension is applied with the curtain-coating method with a coater operating speed of at least approximately 400 m/min. The so-called curtain-coating process is known to the person skilled in the art and is characterized by the following criteria:

In the curtain-coating method, a freely falling curtain of a layering dispersion is formed. The laying dispersion in the form of a thin layer (curtain) is "poured" on a substrate through free fall to apply the layering dispersion to the substrate. DE 10196052 T1 discloses the use of the curtain-coating method in producing information recording materials, among others also heat-sensitive recording materials, wherein multilayer recording layers are created by applying the curtain comprising multiple layering dispersion films to substrates (max. speed 200 m/min).

Setting the coater operating speed to at least approximately 400 m/min has both economic and technical advantages. The operating speed is particularly preferably at least approximately 750 m/min, very particularly preferably at least approximately 1000 m/min and very particularly preferably at least approximately 1500 m/min. It was particularly surprising that even at the last speed, the resulting heat-sensitive recording material was in no way impaired and that the operations were performed optimally even at this high speed.

In a preferred embodiment of the method according to the invention, the aqueous deaerated application suspension has a viscosity of approximately 150 to approximately 800 mPas (Brookfield, 100 rpm, 20° C.). If the value drops below approximately 150 mPas or exceeds approximately 800 mPas, this leads to the coating mass in the coating aggregate running poorly. The viscosity of the aqueous deaerated application suspension is particularly preferably approximately 200 to approximately 500 mPas.

In a preferred embodiment, the surface tension of the aqueous application suspension may be set at approximately 25 to approximately 60 mN/m, preferably at approximately 35 to approximately 50 mN/m (measured according to the static ring method according to Du Noüy, DIN 53914) to optimize the method. The heat-sensitive color-forming layer can be formed online or in a separate coating process offline. This also applies for layers or interlayers that may be applied later.

It is advantageous if the dried heat-sensitive color-forming layer is subjected to a smoothing measure. The surface of the recording material is preferably smoothed with a shoe calendar pursuant to DE 102004029261 B4. It is advantageous thereby to set the Bekk smoothness, measured according to ISO 5627, to approximately 100 to approximately 1000 sec, advantageously to approximately 250 to approximately 600 sec.

The surface roughness (PPS) according to ISO 8791-4 is in the range of approximately 0.50 to approximately 2.50 µm, preferably between 1.00 and 2.00 µm.

The preferred embodiments described in connection with the compound of the formula (I) are also valid for the method according to the invention for producing the heat-sensitive recording material according to the invention.

The present invention also relates to a heat-sensitive recording material, which can be created with the method described above.

The method described above is advantageous from an economic standpoint and allows for a high conduct of proceedings of the coater even at a speed of more than 1500 m/min without bringing about hindrances in the process works, i.e. of the heat-sensitive recording material according to the invention. The conduct of proceedings may take place online or offline, which results in a desirable flexibility.

The heat-sensitive recording material according to the invention is phenol-free and well suited for POS (point of sale) and/or label uses. It is also well suited to the production of parking tickets, transportation tickets, admission tickets, lottery tickets, betting slips, etc., which may be printed using a direct thermal method, and guarantees high durability of the images printed thereupon during long-term storage, even under intensified weather conditions with regard to temperature and ambient humidity and when the typeface comes into contact with hydrophobic substances, e.g. plasticizers, fatty or oily substances, etc.

It has surprisingly been shown that it is possible to obtain heat-sensitive recording materials with the color developer of the formula (I) characterized by excellent durability of the typeface against hydrophobic agents. Good dynamic pressure sensitivities are also achieved.

Without being bound thereto, it is suspected that the stability of the color complex obtained with the compound or the color developer of the formula (I) may be achieved in that the sulfonamide unit —$SO_2$—NH—$Ar^1$ generates additional hydrogen bond donor abilities for the stabilization of the color complex, wherein the possibility of modulating the acidity of this structural unit through adequately substituted radicals $Ar^1$ takes on particular importance.

The invention is described in detail below using non-limiting examples.

EXAMPLES

Production of the compounds of the formula (I) according to the invention.

The compounds I-XXXII (Table 2) were produced as follows:

Step A—Production of the Nitro Arylsulfonanilide

To a mixture of 55 mmol aromatic amine and 50 mmol pyridine is added 50 mmol of the nitro arylsulfonylchloride in portions while stirring. The mixture is heated to 95-100° C. for a short time (5-10 min), cooled and brayed with 100-150 ml of hydrochloric acid (2 mol/l). After collection, it is neutrally washed with water and dried. The nitro arylsulfonanilides were used without previous filtration in Step B.

Step B—Reduction of the Nitro Group to a Primary Amine 40 mmol of the product from Step A are dissolved in 140 ml of ethyl acetate, mixed with 140 mmol $SnCl_2 \cdot 2H_2O$ while stirring and heated during the return flow. The course of the reaction is followed on TLC (eluent: cyclohexane/ethyl acetate 1:1). After ending the reaction (approx. 2-3 h), it is thinned with 140 ml ethyl acetate, mixed with a 10% aqueous $K_2CO_3$ solution and stirred at room temperature for 30 min. The Sn compounds are filtered out and the aqueous separated from the organic phase in the filtrate. The organic phase is extracted twice with 100 ml each time of a saturated sodium chloride solution and subsequently dried over $MgSO_4$. After rotating off the solvent, the amino arylsulfanilide is left in a solid state. Filtration takes place through recrystallization from aqueous methanol.

Step C—Production of the Sulfonylurea Compounds 15 mmol of the product from Step B are dissolved in methylene dichloride (60-100 ml) and added in portions to 15 mmol sulfonyl isocyanate while stirring at room temperature. The course of the reaction is followed on TLC (eluent: n-hexane/$CHCl_3$/$CH_3OH$ 4:2:1). After ending the reaction, the precipitated product is filtered out, washed with methylene dichloride and dried at <70° C.

Compounds XXXIII-XXXIV (Table 2) were converted, starting with the corresponding bis-amine sulfonylchlorides (schema 2, G. Barnikow, K. Krüger, G. Hilgetag, Z. Chem., 6, (7), 262 (1966)), following the general provision of Step A, into bis-amino benzene bis-sulfonanilides and these were converted, following the provision of Step C, into the final products.

The production of the starting compound is known and these are commercially available.

TABLE 2

Compilation of chosen compounds of the formula (I)

| | Y | $Ar^1$ | $Ar^2$ | m | n |
|---|---|---|---|---|---|
| I | 1,2-phenylene | $C_6H_5$ | $C_6H_5$ | 1 | 1 |
| II | 1,2-phenylene | 2-$CH_3$—$C_6H_4$ | $C_6H_5$ | 1 | 1 |
| III | 1,2-phenylene | 4-$CH_3$—$C_6H_4$ | $C_6H_5$ | 1 | 1 |
| IV | 1,2-phenylene | 4-$OCH_3$—$C_6H_4$ | $C_6H_5$ | 1 | 1 |
| V | 1,2-phenylene | 2-($CO_2C_2H_5$)—$C_6H_4$ | $C_6H_5$ | 1 | 1 |
| VI | 1,2-phenylene | 4-($CO_2CH_3$)—$C_6H_4$ | $C_6H_5$ | 1 | 1 |
| VII | 1,2-phenylene | 3-Cl—$C_6H_4$ | $C_6H_5$ | 1 | 1 |
| VIII | 1,2-phenylene | 2-(NH—CO—NH—$C_6H_5$)—$C_6H_4$ | $C_6H_5$ | 1 | 1 |
| IX | 1,2-phenylene | $C_6H_5$ | 4-$CH_3$—$C_6H_4$ | 1 | 1 |
| X | 1,2-phenylene | 2-$CH_3$—$C_6H_4$ | 4-$CH_3$—$C_6H_4$ | 1 | 1 |
| XI | 1,2-phenylene | 4-$CH_3$—$C_6H_4$ | 4-$CH_3$—$C_6H_4$ | 1 | 1 |
| XII | 1,2-phenylene | 3-$CH_3$—$C_6H_4$ | 4-$CH_3$—$C_6H_4$ | 1 | 1 |
| XIII | 1,2-phenylene | 4-$OCH_3$—$C_6H_4$ | 4-$CH_3$—$C_6H_4$ | 1 | 1 |
| XIV | 1,2-phenylene | 2-($CO_2C_2H_5$)—$C_6H_4$ | 4-$CH_3$—$C_6H_4$ | 1 | 1 |
| XV | 1,2-phenylene | 4-($CO_2CH_3$)—$C_6H_4$ | 4-$CH_3$—$C_6H_4$ | 1 | 1 |
| XVI | 1,2-phenylene | 2-Cl—$C_6H_4$ | 4-$CH_3$—$C_6H_4$ | 1 | 1 |
| XVII | 1,2-phenylene | 3-Cl—$C_6H_4$ | 4-$CH_3$—$C_6H_4$ | 1 | 1 |
| XVIII | 1,2-phenylene | 4-Cl—$C_6H_4$ | 4-$CH_3$—$C_6H_4$ | 1 | 1 |
| XIX | 1,2-phenylene | 4-$OC_2H_5$—$C_6H_4$ | 4-$CH_3$—$C_6H_4$ | 1 | 1 |
| XX | 1,2-phenylene | 2-$OCH_3$—$C_6H_4$ | 4-$CH_3$—$C_6H_4$ | 1 | 1 |
| XXI | 1,2-phenylene | 3-(O—$SO_2$—$C_6H_4$-4-$CH_3$)—$C_6H_4$ | 4-$CH_3$—$C_6H_4$ | 1 | 1 |
| XXII | 1,2-phenylene | 2-(NH—CO—NH—$C_6H_5$)—$C_6H_4$ | 4-$CH_3$—$C_6H_4$ | 1 | 1 |
| XXIII | 1,2-phenylene | 4-($CO_2C_2H_5$)—$C_6H_4$ | 4-$CH_3$—$C_6H_4$ | 1 | 1 |
| XXIV | 1,3-phenylene | $C_6H_5$ | 4-$CH_3$—$C_6H_4$ | 1 | 1 |

TABLE 2-continued

Compilation of chosen compounds of the formula (I)

|   | Y | Ar¹ | Ar² | m | n |
|---|---|---|---|---|---|
| XXV | 1,3-phenylene | 2-(NH—CO—NH—$C_6H_5$)—$C_6H_4$ | 4-$CH_3$—$C_6H_4$ | 1 | 1 |
| XXVI | 1,4-phenylene | $C_6H_5$ | 4-$CH_3$—$C_6H_4$ | 1 | 1 |
| XXVII | 1,4-phenylene | 3—$CH_3$—$C_6H_4$ | 4-$CH_3$—$C_6H_4$ | 1 | 1 |
| XXVIII | 1,4-phenylene | 4-($CO_2C_2H_5$)—$C_6H_4$ | 4-$CH_3$—$C_6H_4$ | 1 | 1 |
| XXIX | 1,4-phenylene | 4-Cl—$C_6H_4$ | 4-$CH_3$—$C_6H_4$ | 1 | 1 |
| XXX | 1,4-phenylene | 2-(NH—CO—NH—$C_6H_5$)—$C_6H_4$ | 4-$CH_3$—$C_6H_4$ | 1 | 1 |
| XXXI | 1,4-phenylene | 4-($CO_2C_2H_5$)—$C_6H_4$ | 4-$CH_3$—$C_6H_4$ | 1 | 1 |
| XXXII | Benzene-1,2,4-triyl | $C_6H_5$ | 4-$CH_3$—$C_6H_4$ | 1 | 2 |
| XXXIII | Benzene-1,3,4,6-tetryl | $C_6H_5$ | $C_6H_5$ | 2 | 2 |
| XXXIV | Benzene-1,3,4,6-tetryl | $C_6H_5$ | 4-$CH_3$—$C_6H_4$ | 2 | 2 |
| XXXV | Benzene-1,3,4,6-tetryl | 4-($CO_2C_2H_5$)—$C_6H_4$ | 4-$CH_3$—$C_6H_4$ | 2 | 2 |

Analytical Data:

I, $C_{19}H_{17}N_3O_5S_2$, M=431.5, N-phenyl-2-(3-(phenylsulfonyl)ureide)benzene sulfonamide MS (ESI): m/z (%)=430.0 (13) [M—H]⁻, 273.0 (100) [M-H—$Ar^2SO_2NH_2$]⁻, 247.0 (6) [M-H—$Ar^2SO_2NCO$]⁻.

¹H NMR (500 MHz, DMSO-$d_6$): δ(ppm)=11.71 (1H, s), 10.37 (1H, s), 8.72 (1H, s), 8.04-7.97 (2H, m,), 7.77 (1H, dd, J=8.3=1.2 Hz), 7.73 (1H, dd, J=8.1, 1.7 Hz) 7.71 (1H, tt, J=7.4, 1.5 Hz), 7.67-7.62 (2H, m), 7.49 (1H, ddd, J=8.3, 7.4, 1.6 Hz), 7.21-7.13 (3H, m), 7.02-6.97 (3H, m).

¹³C NMR (126 MHz, DMSO-$d_6$): δ(ppm)=149.06 (NH$\underline{C}$(O)NH), 139.71, 136.65, 135.21, 133.62, 133.40, 131.67, 129.09, 129.04, 128.96, 128.82, 127.34, 125.52, 124.59, 120.54.

II, $C_{20}H_{19}N_3O_5S_2$, M=445.5, N-(2-tolyl)-2-(3-(phenylsulfonyl)ureide)benzene sulfonamide MS (ESI): m/z (%)=444.0 (20) [M-H]⁻, 287.0 (100), [M-H—$Ar^2SO_2NH_2$]⁻, 261.1 (10) [M-H—$Ar^2SO_2NCO$]⁻.

¹H NMR (500 MHz, DMSO-$d_6$): δ(ppm)=11.73 (1H, s), 9.73 (1H, s), 8.74 (1H, s), 8.00-7.98 (2H, m), 7.83 (1H, dd, J=8.5, 1.1 Hz), 7.70 (1H, tt, J=7.4, 1.6 Hz), 7.66-7.60 (3H, m), 7.51 (1H, ddd, J=8.3, 7.6, 1.7 Hz), 7.13 (1H, ddd, J=7.6, 1.1 Hz), 7.05 (1H, ddd, J=8.1, 6.5, 2.2 Hz), 7.03-6.97 (3H, m), 1.95 (3H, s).

¹³C NMR (126 MHz, DMSO-$d_6$): δ(ppm)=148.96 (NH$\underline{C}$(O)NH), 139.78, 135.17, 134.24, 133.72, 133.57, 133.35, 130.68, 129.01, 128.90, 128.43, 127.31, 126.81, 126.56, 126.29, 123.41, 122.77, 17.24 ($\underline{C}H_3$).

III, $C_{20}H_{19}N_3O_5S_2$, M=445.5, N-(4-tolyl)-2-(3-(phenylsulfonyl)ureide)benzene sulfonamide MS (ESI): m/z (%)=287.0 (100) [M-H—$Ar^2SO_2NH_2$]⁻, 261.1 (5) [M-H—$Ar^2SO_2NCO$]⁻.

¹H NMR (500 MHz, DMSO-$d_6$): δ(ppm)=11.74 (1H, s), 10.23 (1H, s), 8.75 (1H, s), 8.04-7.99 (2H, m), 7.78 (1H, dd, J=8.4, 1.1 Hz), 7.71 (1H, dd, 8.0, 1.6 Hz), 7.70 (1H, tt, J=7.4, 1.5 Hz), 766-7.61 (2H, m) 7.46 (1H, ddd, J=8.4, 7.4, 1.6 Hz), 7.14 (1H, ddd, J=7.8, 7.5, 1.2 Hz), 7.00-6.94 (2H, m), 6.93-6.89 (2H, m), 2.14 (3H, s).

¹³C NMR (126 MHz, DMSO-$d_6$): δ(ppm)=149.11 (NH$\underline{C}$(O)NH), 139.81, 135.28, 134.11, 133.96, 133.54, 133.38, 129.58, 129.06, 129.01, 127.88, 127.35, 123.66, 123.32, 121.14, 20.25, ($\underline{C}H_3$).

IV, $C_{20}H_{19}N_3O_6S_2$, M=461.5, N-(4-methoxyphenyl)-2-(3-(phenylsulfonyl)ureide)benzene sulfonamide MS (ESI): m/z (%)=460.0 (25) [M-H]⁻, 303.0 (100) [M-H—$Ar^2SO_2NH_2$]⁻, 278.0 (4) [M-H—$Ar^2SO_2NCO$]⁻.

¹H NMR (500 MHz, DMSO-$d_6$): δ(ppm)=11.75 (1H, s), 10.06 (1H, s), 8.76 (1H, s), 8.02-7.99 (2H, m), 7.78 (1H, dd, J=8.4, 1.2 Hz), 7.70 (1H, tt, J=7.4, 1.6 Hz), 7.67-7.61 (3H, m) 7.47 (1H, ddd, J=8.4, 7.4, 1.6 Hz), 7.14 (1H, ddd, J=7.9, 7.4, 1.2 Hz), 6.94-6.90 (2H, m), 6.77-6.72 (2H, m), 3.65 (3H, s).

¹³C NMR (126 MHz, DMSO-$d_6$): δ(ppm)=156.95 ($\underline{C}$—$OCH_3$), 149.14 (NH$\underline{C}$(O)NH), 139.82, 135.27, 133.50, 133.37, 129.06, 129.04, 128.93, 127.78, 127.31, 124.02, 123.60, 123.22, 114.32, 55.09 (O$\underline{C}H_3$).

V, $C_{22}H_{21}N_3O_7S_2$, M=503.5, ethyl 2-(2-(3-(phenylsulfonyl)ureide)phenyl sulfonamide) benzoate MS (ESI): m/z (%)=501.9 (4) [M-H]⁻, 345.1 (100) [M-H—$Ar^2SO_2NH_2$]⁻, 319.0 (15) [M-H—$Ar^2SO_2NCO$]⁻.

¹H NMR (500 MHz, DMSO-$d_6$): δ(ppm)=11.93 (1H, s), 10.73 (1H, s), 8.66 (1H, s), 8.00-7.96 (2H, m), 7.81 (1H, dd, J=8.0, 1.6 Hz), 7.77 (2H, 2xdd, J=8.2, 1.4 Hz), 7.69 (1H, tt, J=7.4, 1.6 Hz), 766-7.61 (2H, m) 7.46 (1H, ddd, J=8.4, 7.4, 1.6 Hz), 7.14 (1H, ddd, J=7.8, 7.5, 1.2 Hz), 7.64-7.59 (2H, m), 7.58-7.46 (3H, m), 7.53 (1H, ddd, J=8.3, 7.4, 1.6), 7.49 (1H, ddd, J=8.3, 7.4, 1.6 Hz), 7.18 (1H, ddd, J=7.7, 7.8, 1.2 Hz), 7.12 (1H, ddd, J=7.9, 7.4, 1.2 Hz), 4.18 (2H, q, J=7.1 Hz), 1.23 (3H, t, J=7.1 Hz).

¹³C NMR (126 MHz, DMSO-$d_6$): δ(ppm)=166.80 ($\underline{C}O_2R$), 149.07 (NH$\underline{C}$(O)NH), 139.74, 138.05, 135.04, 134.32, 134.25, 133.38, 130.87, 129.37, 129.02, 127.24, 127.10, 125.52, 124.24, 123.89, 120.15, 117.87, 61.47 (O$\underline{C}H_2CH_3$), 13.71 (O$CH_2\underline{C}H_3$).

VI, $C_{21}H_{19}N_3O_7S_2$, M=489.5, methyl 4-(2-(3-(phenylsulfonyl)ureide)phenyl sulfonamide) benzoate MS (ESI): m/z (%)=488.0 (26) [M-H]⁻, 331.0 (100) [M-H—$Ar^2SO_2NH_2$]⁻, 305.0 (50) [M-H—$Ar^2SO_2NCO$]⁻.

¹H NMR (500 MHz, DMSO-$d_6$): δ(ppm)=11.68 (1H, s), 10.97 (1H, s), 8.71 (1H, s), 8.0-7.99 (2H, m), 7.80 (1H, dd, J=8.1, 1.6 Hz), 7.79-7.74 (3H, m), 7.71 (1H, tt, J=7.4, 1.3 Hz), 7.67-7.62 (2H, m), 7.51 (1H, ddd, J=8.3, 7.4, 1.6 Hz), 7.20 (1H, ddd, J=7.7, 1.2 Hz), 7.16-7.12 (2H, m), 3.78 (3H, s), 3.35 (1H, q, J=7.0 Hz), 1.07 (2H, t, J=7.0 Hz).

¹³C NMR (126 MHz, DMSO-$d_6$): δ(ppm)=165.47 ($\underline{C}O_2R$), 149.13 (NH$\underline{C}$(O)NH), 141.49, 139.70, 135.17, 133.95, 133.40, 130.52, 129.05, 129.00, 127.99, 127.34, 125.54, 124.87, 124.05, 118.43, 51.84 (O$\underline{C}H_3$).

VII, $C_{19}H_{16}ClN_3O_5S_2$, M=465.9, N-(3-chlorophenyl)-2-(3-(phenylsulfonyl)ureide) benzene sulfonamide MS (ESI): m/z (%)=307.0 (100) [M-H—$Ar^2SO_2NH_2$]⁻, 281.0 (26) [M-H—$Ar^2SO_2NCO$]⁻.

¹H NMR (500 MHz, DMSO-$d_6$): δ(ppm)=11.70 (1H, s), 10.67 (1H, s), 8.71 (1H, s), 8.02-7.99 (2H, m), 7.77 (1H, dd, J=8.4, 1.2 Hz), 7.76 (2H, dd, J=8.0, 1.6 Hz) 7.70 (1H, tt, J=7.4, 1.3 Hz), 7.66-7.61 (2H, m), 7.52 (1H, ddd, J=8.4 7.3, 1.6 Hz), 7.22 (1H, ddd, J=9.1, 7.9, 1.7 Hz), 7.18 (1H, dd, J=8.1 Hz), 7.08 (1H, dd, J=2.1 Hz), 7.03 (1H, ddd, J=8.0, 2.1, 0.9 Hz)), 6.97 (1H, ddd, J=8.2, 2.1, 0.9 Hz). ¹³C NMR (126 MHz, DMSO-d$_6$): δ(ppm)=149.10 (NH$\underline{C}$(O)NH), 139.71, 138.33, 135.26, 133.90, 133.43, 133.39, 130.76, 129.04, 128.88, 127.80, 127.31, 124.30, 123.97, 123.83, 119.76, 118.5.

VIII, C$_{26}$H$_{23}$N$_5$O$_6$S$_2$, M=565.6, 2-(3-(phenylsulfonyl)ureide)-N-(2-(3-phenylureido)phenyl)benzene sulfonamide MS (ESI): m/z (%)=564.1 (100) [M-H]$^-$, 407.0 (80) [M-H—Ar$^2$SO$_2$NH$_2$]$^-$, 381.2 (12) [M-H—Ar$^2$SO$_2$NCO]$^-$.

$^1$H NMR (500 MHz, DMSO-d$_6$): δ(ppm)=11.74 (1H, s), 9.78 (1H, s), 9.47 (1H, s), 8.72 (1H, s), 8.00 (1H, dd, J=8.3, 1.4 Hz), 8.00-7.97 (2H, m), 7.84 (1H, dd, J=8.3, 1.2 Hz), 7.70 (1H, tt, J=7.5, 1.6 Hz), 7.66 (1H, dd, J=8.0, 1.6 Hz), 7.65-7.62 (2H, m), 7.58-7.54 (1H, m) 7.54-7.51 (2H, m), 7.34-7.29 (2H, m), 7.17 (1H, ddd, J=8.0, 7.2, 0.9 Hz), 7.05 (1H, ddd, J=8.3, 7.4, 1.6 Hz), 7.00 (1H, tt, J=7.4, 1.1 Hz), 6.67 (1H, ddd, J=7.8, 6.4, 1.5 Hz), 6.42 (1H, dd, J=8.0, 1.5 Hz).

$^{13}$C NMR (126 MHz, DMSO-d$_6$): δ(ppm)=152.67 (NH$\underline{C}$(O)NH), 149.17 (NH$\underline{C}$(O)NH), 139.80, 139.67, 136.96, 135.56, 133.39, 131.70, 129.06, 128.85, 128.78, 128.74, 127.54, 127.33, 125.55, 124.14, 123.03, 122.18, 121.96, 121.15, 118.33, 118.31.

IX, C$_{20}$H$_{19}$N$_3$O$_5$S$_2$, M=445.5, N-phenyl-2-(3-tosylureide)benzene sulfonamide MS (ESI): m/z (%)=444.0 (22) [M-H]$^-$, 273.0 (100) [M-H—Ar$^2$SO$_2$NH$_2$]$^-$, 247.0 (9) [M-H—Ar$^2$SO$_2$NCO]$^-$.

$^1$H NMR (500 MHz, DMSO-d$_6$): δ(ppm)=11.65 (1H, s), 10.38 (1H, s), 8.72 (1H, s), 7.92-7.87 (2H, m), 7.79 (1H, dd, J=8.4, 1.1 Hz), 7.74 (1H, dd, J=8.0, 1.6 Hz), 7.48 (1H, ddd, J=8.4, 7.3, 1.6 Hz), 7.44-7.40 (2H, m), 7.26-7.12 (3H, m), 7.05-7.01 (2H, m), 6.99 (1H, tt, J=7.4, 1.4 Hz), 2.38 (3H, s).

$^{13}$C NMR (126 MHz, DMSO-d$_6$): δ(ppm)=149.11 (NH$\underline{C}$(O)NH), 143.93, 136.91, 136.70, 135.31, 133.61, 129.46, 129.10, 128.97, 127.88, 127.45, 124.60, 123.69, 123.44, 120.54, 20.99 ($\underline{C}$H$_3$).

X, C$_{21}$H$_{21}$N$_3$O$_5$S$_2$, M=459.5, N-(2-tolyl)-2-(3-tosylureide)benzene sulfonamide MS (ESI): m/z (%)=457.9 (1) [M-H]$^-$, 287.1 (100) [M-H—Ar$^2$SO$_2$NH$_2$]$^-$, 261.1 (16) [M-H—Ar$^2$SO$_2$NCO]$^-$.

$^1$H NMR (500 MHz, DMSO-d$_6$): δ(ppm)=11.61 (1H, s), 9.69 (1H, s), 8.70 (1H, s), 7.87-7.80 (2H, m), 7.82 (1H, dd, J=8.3, 1.1 Hz) 7.60 (1H, dd, J=8.0, 1.6 Hz), 7.52 (1H, ddd, J=8.4, 7.3, 1.6 Hz), 7.45-7.40 (2H, m), 7.25-7.19 (1H, m), 7.14 (1H, ddd, J=8.0, 7.4, 1.1 Hz), 7.09-7.05 (1H, m), 7.03-7.00 (2H, m), 6.97-6.94 (1H, m), 2.40 (3H, s), 1.95 (3H, s)

$^{13}$C NMR (126 MHz, DMSO-d$_6$): δ(ppm)=149.00 (NH$\underline{C}$(O)NH), 143.85, 136.95, 135.23, 134.22, 133.74, 133.56, 130.69, 129.42, 128.90, 128.38, 127.36, 126.78, 126.48, 126.28, 123.35, 122.74, 20.98 ($\underline{C}$H$_3$), 17.26 ($\underline{C}$H$_3$).

XI, C$_{21}$H$_{21}$N$_3$O$_5$S$_2$, M=459.5, N-(4-tolyl)-2-(3-tosylureide)benzene sulfonamide MS (ESI): m/z (%)=287.1 (100) [M-H—Ar$^2$SO$_2$NH$_2$]$^-$, 261.1 (8) [M-H—Ar$^2$SO$_2$NCO]$^-$.

$^1$H NMR (500 MHz, DMSO-d$_6$): δ(ppm)=11.63 (1H, s), 10.20 (1H, s), 8.71 (1H, s), 7.90-7.86 (2H, m), 7.79 (1H, dd, J=8.4, 1.2 Hz), 7.70 (1H, dd, J=8.0, 1.6 Hz), 7.47 (1H, ddd, J=8.4, 7.4, 1.6 Hz), 7.44-7.41 (2H, m), 7.14 (1H, ddd, J=8.0, 7.3, 1.2 Hz), 6.97-6.94 (2H, m,), 6.91-6.88 (2H, m), 2.39 (3H, s), 2.15 (3H, s).

$^{13}$C NMR (126 MHz, DMSO-d$_6$): δ(ppm)=149.06 (NH$\underline{C}$(O)NH), 143.84, 136.95, 135.33, 134.00, 133.95, 133.48, 129.52, 129.44, 128.96, 127.78, 127.41, 123.55, 123.23, 121.05, 20.95 ($\underline{C}$H$_3$), 20.20 ($\underline{C}$H$_3$).

XII, C$_{21}$H$_{21}$N$_3$O$_5$S$_2$, M=459.5, N-(3-tolyl)-2-(3-tosylureide)benzene sulfonamide MS (ESI): m/z (%)=58.0 (1) [M-H]$^-$, 287.1 (100) [M-H—Ar$^2$SO$_2$NH$_2$]$^-$, 261.0 (10) [M-H—Ar$^2$SO$_2$NCO]$^-$.

$^1$H NMR (500 MHz, DMSO-d$_6$): δ(ppm)=11.64 (1H, s), 10.29 (1H, s), 8.72 (1H, s), 7.90-7.86 (2H, m), 7.79 (1H, dd, J=8.4, 1.1 Hz), 7.74 (1H, dd, J=8.0, 1.6 Hz), 7.48 (1H, ddd, J=8.4, 7.4, 1.6 Hz), 7.42 (2H, d, J=8.1 Hz), 7.17 (1H, ddd, J=7.7, 1.2 Hz), 7.03 (1H, t, J=7.8 Hz), 6.86 (1H, t, J=1.9 Hz), 6.82-6.78 (2H, m), 2.38 (3H, s), 2.15 (3H, s).

$^{13}$C NMR (126 MHz, DMSO-d$_6$): δ(ppm)=149.05 (NH$\underline{C}$(O)NH), 143.89, 138.55, 136.92, 136.60, 135.36, 133.56, 129.44, 128.89, 127.84, 127.39, 125.37, 123.63, 123.23, 121.12, 117.65, 20.97 ($\underline{C}$H$_3$), 20.85 ($\underline{C}$H$_3$).

XIII, C$_{21}$H$_{21}$N$_3$O$_6$S$_2$, M=475.5, N-(4-methoxyphenyl)-2-(3-tosylureide)benzene sulfonamide MS (ESI): m/z (%)=473.9 (2) [M-H]$^-$, 303.0 (100) [M-H—Ar$^2$SO$_2$NH$_2$]$^-$, 277.0 (5) [M-H—Ar$^2$SO$_2$NCO]$^-$.

$^1$H NMR (500 MHz, DMSO-d$_6$): δ(ppm)=11.64 (1H, s), 10.03 (1H, s), 8.72 (1H, s), 7.89-7.85 (2H, m), 7.79 (1H, dd, J=8.4, 1.1 Hz), 7.64 (1H, dd, J=8.0, 1.6 Hz), 7.48 (1H, ddd, J=8.4, 7.3, 1.6 Hz), 7.44-7.40 (2H, m), 7.14 (1H, ddd, J=7.9, 7.5, 1.2 Hz), 6.93-6.88 (2H, m), 6.75-6.71 (2H, m) 3.66 (3H, s), 2.39 (3H, s).

$^{13}$C NMR (126 MHz, DMSO-d$_6$): δ(ppm)=156.89 (C—O$\underline{C}$H$_3$), 149.10 (NH$\underline{C}$(O)NH), 143.84, 136.96, 135.32, 133.45, 129.45, 129.42, 128.92, 127.68, 127.36, 123.94, 123.50, 123.13, 114.26, 55.04 (O$\underline{C}$H$_3$), 20.95 ($\underline{C}$H$_3$).

XIV, C$_{23}$H$_{23}$N$_3$O$_7$S$_2$, M=517.6, ethyl 2-(2-(3-tosylureido)phenyl sulfonamide) benzoate MS (ESI): m/z (%)=516.0 (5) [M-H]$^-$, 345.0 (100) ([M-H—Ar$^2$SO$_2$NH$_2$]$^-$, 319.1 (23) [M-H—Ar$^2$SO$_2$NCO]$^-$.

$^1$H NMR (500 MHz, DMSO-d$_6$): δ(ppm)=11.84 (1H, s), 10.73 (1H, s), 8.64 (1H, s), 7.87-7.84 (2H, m), 7.82 (1H, dd, J=8.0, 1.7 Hz), 7.78 (1H, dd, J=8.2, 1.1 Hz), 7.77 (1H, dd, J=7.9, 1.6 Hz), 7.53 (1H, ddd, J=8.3, 7.5, 1.6 Hz), 7.49 (1H, ddd, J=8.4, 7.2, 1.7 Hz), 7.41 (1H, dd, J=8.3, 1.1 Hz), 7.40-7.38 (2H, m), 7.18 (1H, ddd, J=7.8, 7.6, 1.2 Hz), 7.13 (1H, ddd, J=7.8, 7.5, 1.3 Hz), 4.19 (2H, q, J=7.1 Hz), 2.37 (3H, s), 1.24 (3H, t, J=7.1 Hz).

$^{13}$C NMR (126 MHz, DMSO-d$_6$): δ(ppm)=166.78 ($\underline{C}$O$_2$R), 149.07 (NH$\underline{C}$(O)NH), 143.86, 138.08, 136.91, 135.09, 134.29, 134.23, 130.85, 129.39, 129.33, 127.31, 127.07, 124.17, 123.86, 123.82, 120.06, 117.81, 61.45 (O$\underline{C}$H$_2$CH$_3$), 20.93 ($\underline{C}$H$_3$), 13.70 (OCH$_2$$\underline{C}$H$_3$).

XV, C$_{22}$H$_{21}$N$_3$O$_7$S$_2$, M=503.5, methyl 4-(2-(3-tosylureide)phenyl sulfonamide) benzoate MS (ESI): m/z (%)=502.0 (1) [M-H]$^-$, 331.0 (100) [M-H—Ar$^2$SO$_2$NH$_2$]$^-$, 305.1 (73) [M-H—Ar$^2$SO$_2$NCO]$^-$.

$^1$H NMR (500 MHz, DMSO-d$_6$): δ(ppm)=11.55 (1H, s), 10.93 (1H, s), 8.67 (1H, s), 7.90-7.86 (2H, m), 7.81 (1H, dd, J=8.2, 1.6 Hz), 7.76 (1H, dd, J=8.5, 1.2 Hz), 7.76-7.72 (2H, m), 7.51 (1H, ddd, J=8.4, 7.3, 1.6 Hz), 7.43-7.41 (2H, m), 7.20 (1H, ddd, J=7.9, 7.4, 1.2 Hz), 7.09 (2H, m), 3.77 (3H, s), 2.39 (3H, s).

$^{13}$C NMR (126 MHz, DMSO-d$_6$): δ(ppm)=165.45 ($\underline{C}$O$_2$R), 149.13 (NH$\underline{C}$(O)NH), 143.97, 141.46, 136.80, 135.14, 133.96, 130.51, 129.47, 129.07, 127.99, 127.50, 124.81, 124.18, 124.05, 118.31, 51.84 (O$\underline{C}$H$_3$), 20.96 ($\underline{C}$H$_3$).

XVI, C$_{20}$H$_{18}$ClN$_3$O$_5$S$_2$, M=479.9, N-(2-chlorophenyl)-2-(3-tosylureide)benzene sulfonamide MS (ESI): m/z (%)=307.0 (100) [M-H—Ar$^2$SO$_2$NH$_2$]$^-$, 281.0 (90) [M-H—Ar$^2$SO$_2$NCO]$^-$.

$^1$H NMR (500 MHz, DMSO-d$_6$): δ(ppm)=11.64 (1H, s), 10.00 (1H, s), 8.65 (1H, s), 7.89 (1H, dd, J=8.5, 1.2 Hz), 7.87-7.83 (2H, m), 7.64 (1H, dd, J=8.0, 1.6 Hz), 7.52 (1H, ddd, J=8.5, 7.2, 1.5 Hz), 7.41 (2H, d, J=8.0 Hz), 7.32 (1H, dd, J=8.0, 1.5 Hz), 7.27 (1H, dd, J=8.0, 1.7 Hz), 7.22 (1H, ddd, J=7.7, 1.5 Hz), 7.13 (1H, ddd, J=8.1, 7.2, 1.0 Hz), 7.12 (1H, ddd, J=7.7, 1.2 Hz), 2.38 (3H, s)

$^{13}$C NMR (126 MHz, DMSO-$d_6$): δ(ppm)=148.94 (NH$\underline{C}$(O)NH), 143.89, 136.86, 135.37, 133.89, 132.51, 129.81, 129.43, 129.01, 128.96, 127.94, 127.90, 127.69, 127.38, 127.25, 123.34, 122.73, 20.99 ($\underline{C}H_3$).

XVII, $C_{20}H_{18}ClN_3O_5S_2$, M=479.9, N-(3-chlorphenyl)-2-(3-tosylureide)benzene sulfonamide MS (ESI): m/z (%)=477.9 (2) [M-H]$^-$, 307.0 (100) [M-H—Ar$^2$SO$_2$NH$_2$]$^-$, 281.0 (40) [M-H—Ar$^2$SO$_2$NCO]$^-$.

$^1$H NMR (500 MHz, DMSO-$d_6$): δ(ppm)=11.63 (1H, s), 10.68 (1H, s), 8.70 (1H, s), 7.90-7.87 (2H, m), 7.78 (1H, dd, J=8.5, 1.2 Hz), 7.76 (1H, dd, J=8.0, 1.6 Hz), 7.51 (1H, ddd, J=8.4, 7.4, 1.6 Hz), 7.43-7.39 (2H, m), 7.19 (1H, ddd, J=8.1, 7.4, 1.2 Hz), 7.18 (1H, dd, J=8.2 Hz), 7.08 (1H, dd, J=2.1 Hz), 7.04 (1H, ddd, J=8.1, 2.1, 0.9 Hz), 6.99 (1H, ddd, J=8.2, 2.2, 0.9 Hz), 2.37 (3H, s)

$^{13}$C NMR (126 MHz, DMSO-$d_6$): δ(ppm)=149.14 (NH$\underline{C}$(O)NH), 143.91, 138.37, 136.90, 135.35, 133.88, 133.46, 130.75, 129.45, 128.90, 127.77, 127.40, 124.29, 123.90, 123.81, 119.76, 118.55, 20.98 ($\underline{C}H_3$).

XVIII, $C_{20}H_{18}ClN_3O_5S_2$, M=479.9, N-(4-chlorphenyl)-2-(3-tosylureide)benzene sulfonamide MS (ESI): m/z (%)=307.0 (100) [M-H—Ar$^2$SO$_2$NH$_2$]$^-$, 281.0 (23) [M-H—Ar$^2$SO$_2$NCO]$^-$.

$^1$H NMR (500 MHz, DMSO-$d_6$): δ(ppm)=11.63 (1H, s), 10.56 (1H, s), 8.72 (1H, s), 7.91-7.86 (2H, m), 7.78 (1H, dd, J=8.4, 1.1 Hz), 7.72 (1H, dd, J=8.0, 1.5 Hz), 7.50 (1H, ddd, J=8.4, 7.4, 1.6 Hz), 7.42 (2H, d, J=8.0 Hz), 7.22-7.15 (3H, m), 7.02-7.00 (2H, m), 2.38 (3H, s)

$^{13}$C NMR (126 MHz, DMSO-$d_6$): δ(ppm)=149.15 (NH$\underline{C}$(O)NH), 143.91, 136.88, 135.76, 135.27, 133.78, 129.48, 129.46, 129.07, 128.94, 128.70, 127.74, 127.43, 123.75, 121.92, 20.98 ($\underline{C}H_3$).

XIX, $C_{22}H_{23}N_3O_6S_2$, M=489.5, N-(4-ethoxyphenyl)-2-(3-tosylureide)benzene sulfonamide MS (ESI): m/z (%)=488.0 (3) [M-H]$^-$, 317.1 (100) [M-H—Ar$^2$SO$_2$NH$_2$]$^-$.

$^1$H NMR (500 MHz, DMSO-$d_6$): δ(ppm)=11.66 (1H, s), 10.03 (1H, s), 8.74 (1H, s), 7.90-7.86 (2H, m), 7.80 (1H, dd, J=8.4, 1.2 Hz), 7.65 (1H, dd, J=8.0, 1.6 Hz), 7.48 (1H, ddd, J=8.4, 7.4, 1.6 Hz), 7.45-7.41 (2H, m), 7.14 (1H, ddd, J=7.9, 7.5, 1.2 Hz), 6.93-6.88 (2H, m), 6.75-6.71 (2H, m), 3.91 (2H, q, J=7.0 Hz), 2.39 (3H, s), 1.26 (3H, t, J=7.0 Hz).

$^{13}$C NMR (126 MHz, DMSO-$d_6$): δ(ppm)=156.19 ($\underline{C}$—OC$_2$H$_5$), 149.11 (NH$\underline{C}$(O)NH), 143.82, 136.97, 135.33, 133.43, 129.43, 128.98, 128.81, 127.67, 127.36, 123.92, 123.46, 123.08, 114.73, 63.05 (O$\underline{C}$H$_2$CH$_3$), 20.94 ($\underline{C}H_3$), 14.48 (OCH$_2\underline{C}$H$_3$).

XX, $C_{21}H_{21}N_3O_6S_2$, M=475.5, N-(2-methoxyphenyl)-2-(3-tosylureido)benzene sulfonamide MS (ESI): m/z (%)=473.9 (3) [M-H]$^-$, 303.0 (100) [M-H—Ar$^2$SO$_2$NH$_2$]$^-$, 277.0 (10) [M-H—Ar$^2$SO$_2$NCO]$^-$.

$^1$H NMR (500 MHz, DMSO-$d_6$): δ(ppm)=11.68 (1H, s), 9.42 (1H, s), 8.61 (1H, s), 7.96 (1H, dd, J=8.5, 1.2 Hz), 7.92-7.86 (2H, m), 7.58 (1H, dd, J=7.9, 1.6 Hz), 7.47 (1H, ddd, J=8.5, 7.4, 1.6 Hz), 7.43 (2H, d, J=8.1 Hz), 7.24 (1H, dd, J=7.8, 1.6 Hz), 7.07 (1H, dd, J=5.1, 1.6 Hz), 7.06 (1H, ddd, J=7.8, 5.9, 1.8 Hz), 6.86-6.78 (2H, m), 3.33 (3H, s), 2.38 (3H, s)

$^{13}$C NMR (126 MHz, DMSO-$d_6$): δ(ppm)=152.30 ($\underline{C}$—OCH$_3$), 148.97 (NH$\underline{C}$(O)NH), 143.97, 136.85, 135.40, 133.56, 129.45, 129.13, 127.60, 127.44, 127.17, 125.22, 124.05, 122.82, 121.92, 120.36, 111.56, 55.22 (O$\underline{C}H_3$), 20.97 ($\underline{C}H_3$).

XXI, $C_{27}H_{25}N_3O_8S_2$, M=615.7, 3-(2-(3-tosylureide)phenyl sulfonamide)phenyl 4-methyl benzene sulfonate MS (ESI): m/z (%)=614.1 (100) [M-H]$^-$, 443.0 (95) [M-H—Ar$^2$SO$_2$NH$_2$]$^-$, 417.0 (25) [M-H—Ar$^2$SO$_2$NCO]$^-$.

$^1$H NMR (500 MHz, DMSO-$d_6$): δ(ppm)=11.64 (1H, s), 10.70 (1H, s), 8.68 (1H, s), 7.91-7.85 (2H, m), 7.81 (1H, d, J=8.3 Hz), 7.64 (3H, m), 7.52 (1H, ddd, J=8.5, 7.2, 1.5 Hz), 7.40 (4H, t, J=8.3 Hz,), 7.18 (1H, ddd, J=7.7, 1.2 Hz), 7.13 (1H, dd, J=8.2, Hz), 6.93 (1H, dd, J=8.1, 2.0 Hz), 6.89 (1H, dd, J=2.2 Hz), 6.61 (1H, dd, J=8.1, 2.3 Hz), 2.37 (6H, s).

$^{13}$C NMR (126 MHz, DMSO-$d_6$): δ(ppm)=149.32, 149.19 (NH$\underline{C}$(O)NH), 145.71, 143.88, 138.30, 136.93, 135.33, 133.85, 131.19, 130.46, 130.09, 129.43, 128.77, 127.97, 127.50, 127.37, 125.58, 123.56, 118.57, 117.58, 113.36, 21.08 ($\underline{C}H_3$), 20.96 ($\underline{C}H_3$).

XXII, $C_{27}H_{25}N_5O_6S_2$, M=579.6, 4-methyl-N-((4-(N-(2-(3-phenylureide)phenyl) sulfamoyl)phenyl)carbamoyl)benzene sulfonamide MS (ESI): m/z (%)=578.1 (100) [M-H]$^-$, 407.1 (55), [M-H—Ar$^2$SO$_2$NH$_2$]$^-$, 381.0 (8) [M-H—Ar$^2$SO$_2$NCO]$^-$.

$^1$H NMR (500 MHz, DMSO-$d_6$): δ(ppm)=11.63 (1H, s), 9.75 (1H, s), 9.45 (1H, s), 8.69 (1H, s), 8.30 (1H, s), 8.00 (1H, dd, J=8.4, 1.3 Hz), 7.84 (1H, dd, J=8.4, 1.2 Hz), 7.86-7.83 (2H, m), 7.65 (1H, dd, J=8.0, 1.6 Hz), 7.55 (1H, ddd, J=8.6, 7.2, 1.7 Hz), 7.52-7.49 (2H, m), 7.44-7.40 (2H, m), 7.33-7.29 (2H, m), 7.16 (1H, ddd, J=8.1, 7.2, 1.2 Hz), 7.07 (1H, ddd, J=8.3, 7.4, 1.6 Hz), 7.00 (1H, tt, J=7.4, 1.1 Hz), 6.68 (1H, ddd, J=7.7, 1.5 Hz), 6.40 (1H, dd, J=8.0, 1.6 Hz), 2.40 (3H, s).

$^{13}$C NMR (126 MHz, DMSO-$d_6$): δ(ppm)=152.62 (NH$\underline{C}$(O)NH, 149.17 (NH$\underline{C}$(O)NH), 146.49, 143.86, 141.76, 141.40, 139.63, 136.95, 135.55, 129.43, 129.19, 128.74, 128.70, 127.53, 127.35, 125.56, 124.16, 121.92, 118.54, 118.30, 118.28, 116.84, 20.82 ($\underline{C}H_3$).

XXIII, $C_{27}H_{25}N_3O_7S_2$, M=517.6, ethyl 4-(2-(3-tosylureide)phenyl) sulfonamide)benzoate MS (ESI): m/z (%)=516.9 (4) [M-H]$^-$, 345.0 (100) [M-H—Ar$^2$SO$_2$NH$_2$]$^-$, 319.1 (70) [M-H—Ar$^2$SO$_2$NCO]$^-$.

$^1$H NMR (500 MHz, DMSO-$d_6$): δ(ppm)=11.53 (1H, s), 10.91 (1H, s), 8.66 (1H, s), 7.92-7.87 (2H, m), 7.82 (1H, dd, J=8.0, 1.6 Hz), 7.76 (1H, dd, J=8.4, 1.1 Hz), 7.77-7.72 (2H, m), 7.51 (1H, ddd, J=8.3, 7.4, 1.6 Hz), 7.43 (2H, d, J=8.1 Hz), 7.22-7.18 (1H, m), 7.13-7.10 (2H, m), 4.24 (3H, q, J=7.2 Hz), 2.39 (3H, s), 1.26 (3H, t, J=7.1 Hz)

$^{13}$C NMR (126 MHz, DMSO-$d_6$): δ(ppm)=164.94 ($\underline{C}$O$_2$R), 149.14 (NH$\underline{C}$(O)NH), 143.93, 141.38, 136.82, 135.14, 133.94, 130.45, 129.44, 129.13, 127.98, 127.52, 125.12, 124.18, 124.02, 118.31, 60.45 (O$\underline{C}$H$_2$CH$_3$), 20.96 ($\underline{C}H_3$), 14.06 (OCH$_2\underline{C}$H$_3$).

XXIV, $C_{20}H_{19}N_3O_5S_2$, M=445.5, N-phenyl-3-(3-tosylureide)benzene sulfonamide MS (ESI): m/z (%)=444.0 (100) [M-H]$^-$, 273.1 (20) [M-H—Ar$^2$SO$_2$NH$_2$]$^-$, 247.0 (8) [M-H—Ar$^2$SO$_2$NCO]$^-$.

$^1$H NMR (500 MHz, DMSO-$d_6$): δ(ppm)=10.82 (1H, s), 10.29 (1H, s), 9.17 (1H, s), 8.05-8.02 (1H, m), 7.92-7.88 (2H, m), 7.46 (1H, m), 7.44-7.40 (4H, m), 7.22-7.17 (2H, m), 7.12-7.08 (2H, m), 6.99 (1H, tt, 7.4, 1.2 Hz), 2.36 (3H, s).

$^{13}$C NMR (126 MHz, DMSO-$d_6$): δ(ppm)=149.42 (NH$\underline{C}$(O)NH), 143.95, 140.29, 138.90, 137.58, 137.01, 129.63, 129.48, 129.06, 127.53, 124.05, 122.91, 121.22, 120.13, 116.67, 21.01 ($\underline{C}H_3$).

XXV, $C_{27}H_{25}N_5O_6S_2$, M=579.6, N-(2-(3-phenylureide)phenyl)-3-(3-tosylureide)benzene sulfonamide MS (ESI): m/z (%)=578.1 (95) [M-H]$^-$, 407.1 (100) [M-H—Ar$^2$SO$_2$NH$_2$]$^-$.

¹H NMR (500 MHz, DMSO-d₆): δ(ppm)=9.56 (1H, s), 9.47 (1H, s), 9.16 (1H, s), 8.29 (1H, s), 8.05 (1H, dd, J=8.3, 1.4 Hz), 7.93 (1H, t, J=2.0 Hz, dd), 7.89 (2H, d, J=8.2 Hz), 7.53 (1H, dd, J=8.0, 2.1 Hz), 7.52-7.49 (2H, m), 7.44 (1H, t, J=8.1 Hz), 7.44 (2H, d, J=8.1 Hz) 7.33 (1H, ddd, J=7.8, 1.4 Hz), 7.31-7.27 (2H, m), 7.16 (1H, ddd, J=8.0, 1.6 Hz), 6.98 (1H, t), J=7.3 Hz), 6.76 (1H, ddd, J=7.6, 1.5 Hz), 6.49 (1H, dd, J=8.0, 1.6 Hz), 2.39 (3H, s)

¹³C NMR (126 MHz, DMSO-d₆): δ(ppm)=152.49 (NH$\underline{C}$(O)NH), 149.38 (NH$\underline{C}$(O)NH), 143.91, 139.94, 139.76, 138.78, 136.98, 136.95, 129.47, 129.44, 128.73, 127.58, 127.49, 127.13, 124.88, 122.94, 121.88, 121.84, 121.70, 120.95, 118.25, 117.06, 21.00 ($\underline{C}$H₃).

XXVI, $C_{20}H_{19}N_3O_5S_2$, M=445.5, N-phenyl-4-(3-tosylureide)benzene sulfonamide MS (ESI): m/z (%)=444.1 (100) [M-H]⁻, 273.0 (40) [M-H—Ar²SO₂NH₂]⁻, 247.1 (68) [M-H—Ar²SO₂NCO]⁻.

¹H NMR (500 MHz, DMSO-d₆): δ(ppm)=10.88 (1H, s), 10.11 (1H, s), 9.18 (1H, s), 7.88-7.84 (2H, m), 7.68-7.64 (2H, m), 7.50-7.47 (2H, m), 7.40 (2H, d, J=8.1 Hz), 7.22-7.17 (2H, m), 7.10-7.06 (2H, m), 6.99 (1H, tt, J=7.4, 1.3 Hz), 2.36 (3H, s)

¹³C NMR (126 MHz, DMSO-d₆): δ(ppm)=149.25 (NH$\underline{C}$(O)NH), 143.93, 142.02, 137.71, 136.83, 133.34, 129.44, 129.00, 127.92, 127.47, 123.93, 120.09, 118.51, 20.97 ($\underline{C}$H₃).

XXVII, $C_{21}H_{21}N_3O_5S_2$, M=459.5, N-(3-tolyl)-4-(3-tosylureide)benzene sulfonamide MS (ESI): m/z (%)=458.0 (100) [M-H]⁻, 287.0 (23) [M-H—Ar²SO₂NH₂]⁻, 261.1 (47) [M-H—Ar²SO₂NCO]⁻.

¹H NMR (500 MHz, DMSO-d₆): δ(ppm)=10.84 (1H, s), 10.04 (1H, s), 9.17 (1H, s), 7.89-7.84 (2H, m), 7.69-7.64 (2H, m), 7.51-7.47 (2H, m), 7.42-7.38 (2H, m), 7.07 (1H, t, J=7.7 Hz), 6.92-6.86 (2H, m), 6.80 (1H, ddt, J=7.4, 1.7, 0.9 Hz), 2.37 (3H, s), 2.17 (3H, s)

¹³C NMR (126 MHz, DMSO-d₆): δ(ppm)=149.26 (NH$\underline{C}$(O)NH), 143.93, 141.99, 138.33, 137.67, 136.84, 133.45, 129.44, 129.41, 128.80, 127.91, 127.47, 124.61, 120.48, 118.51, 116.98, 20.95 ($\underline{C}$H₃). 20.93 ($\underline{C}$H₃).

XXVIII, $C_{22}H_{21}N_3O_7S_2$, M=503.5, methyl 4-(4-(3-tosylureide)phenyl sulfonamide)benzoate MS (ESI): m/z (%)=502.0 (100) [M-H]⁻, 331.0 (12) [M-H—Ar²SO₂NH₂]⁻, 305.1 (45) [M-H—Ar²SO₂NCO]⁻.

¹H NMR (500 MHz, DMSO-d₆): δ(ppm)=10.88 (1H, s), 10.70 (1H, s), 9.20 (1H, s), 7.86 (2H, d, J=8.0 Hz), 7.81 (2H, d, J=8.6 Hz), 7.74 (2H, d, J=8.6 Hz), 7.51 (2H, d, J=8.7 Hz), 7.39 (2H, d, J=8.0 Hz), 7.21 (2H, d, J=8.6 Hz), 3.76 (3H, s), 2.35 (3H, s).

¹³C NMR (126 MHz, DMSO-d₆): δ(ppm)=165.58 ($\underline{C}$O₂R), 149.26 (NH$\underline{C}$(O)NH), 143.93, 142.40, 142.37, 136.81, 132.93, 130.49, 129.41, 128.00, 127.46, 124.35, 118.64, 118.16, 51.76 (O$\underline{C}$H₃), 20.95 ($\underline{C}$H₃).

XXIX, $C_{20}H_{18}N_3O_5S_2$, M=479.9, N-(4-chlorphenyl)-4-(3-tosylureido)benzene sulfonamide MS (ESI): m/z (%)=478.0 (100) [M-H]⁻, 306.9 (18) [M-H—Ar²SO₂NH₂]⁻, 281.1 (52) [M-H—Ar²SO₂NCO]⁻.

¹H NMR (500 MHz, DMSO-d₆): δ(ppm)=10.86 (1H, s), 10.27 (1H, s), 9.19 (1H, s), 7.90-7.85 (2H, m), 7.70-7.65 (2H, m), 7.53-7.49 (2H, m), 7.40 (2H, d, J=8.1 Hz), 7.29-7.23 (2H, m), 7.11-7.07 (2H, m), 2.35 (3H, s).

¹³C NMR (126 MHz, DMSO-d₆): δ(ppm)=149.28 (NH$\underline{C}$(O)NH), 143.95, 142.24, 136.84, 136.73, 132.98, 129.43, 129.01, 128.16, 127.96, 127.50, 121.67, 118.59, 20.98 ($\underline{C}$H₃).

XXX, $C_{27}H_{15}N_2O_6S_2$, M=579.6, 4-methyl-N-((4-(N-(4-(3-phenylureide)phenyl)sulfamoyl)phenyl)carbamoyl)benzene sulfonamide MS (ESI): m/z (%)=578.1 (100) [M-H]⁻, 407.0 (18) [M-H—Ar²SO₂NH₂]⁻, 381.0 (4) [M-H—Ar²SO₂NCO]⁻.

¹H NMR (500 MHz, DMSO-d₆): δ(ppm)=10.91 (1H, s), 9.43 (2H, d, J=30.4 Hz), 9.22 (1H, s), 8.28 (1H, s), 8.01 (1H, dd, J=8.2, 1.3 Hz), 7.89 (2H, d, J=8.1 Hz), 7.61 (2H, d, J=8.9 Hz), 7.51 (4H, m), 7.43 (2H, d, J=8.1 Hz), 7.29 (2H, t, J=7.8 Hz), 7.16 (1H, ddd, J=7.8, 1.5 Hz), 6.97 (1H, t, J=7.4 Hz), 6.78 (1H, ddd, J=7.9, 1.4 Hz), 6.50 (1H, d, J=7.9, 1.4 Hz), 2.39 (3H, s).

¹³C NMR (126 MHz, DMSO-d₆): δ(ppm)=152.53 (NH$\underline{C}$(O)NH), 149.26 (NH$\underline{C}$(O)NH), 143.96, 142.18, 139.72, 136.86, 136.83, 133.00, 129.47, 129.43, 128.71, 128.39, 127.52. 125.17, 121.96, 121.85, 120.99, 118.29, 118.28, 118.26, 20.99 ($\underline{C}$H₃).

XXXI, $C_{23}H_{23}N_3O_7S_2$, M=517.6, ethyl 4-(4-(3-tosylureide)phenyl sulfonamide)benzoate MS (ESI): m/z (%)=516.0 (100) [M-H]⁻, 345.0 (12) [M-H—Ar²SO₂NH₂]⁻, 319.0 (43) [M-H—Ar²SO₂NCO]³¹

¹H NMR (500 MHz, DMSO-d₆): δ(ppm)=10.87 (1H, s), 10.69 (1H, s), 9.20 (1H, s), 7.89-7.84 (2H, m), 7.83-7.79 (2H, m), 7.77-7.73 (2H, m), 7.55-7.50 (2H, m), 7.39 (2H, d, J=8.1 Hz), 7.25-7.20 (2H, m), 4.22 (2H, q, J=7.1 Hz), 2.34 (3H, s), 1.24 (3H, t, J=7.1 Hz)

¹³C NMR (126 MHz, DMSO-d₆): δ(ppm)=165.10 ($\underline{C}$O₂R), 149.27 (NH$\underline{C}$(O)NH), 143.93, 142.41, 142.33, 136.83, 132.95, 130.45, 129.41, 128.03, 127.49, 124.68, 118.64, 118.20, 60.38 (O$\underline{C}$H₂CH₃), 20.95 ($\underline{C}$H₃), 14.07 (OCH₂$\underline{C}$H₃).

XXXII, $C_{28}H_{27}N_5O_8S_2$, M=657.7, N,N'-(((4-(N-phenyl sulfamoyl)-1,3-phenylene)bis(azanediyl))bis(carbonyl))bis(4-methyl benzene sulfonamide)

MS (ESI): m/z (%)=656.1 (100) [M-H]⁻, 485.1 (60) [M-H—Ar²SO₂NH₂]⁻, 459.0 (2) [M-H—Ar²SO₂NCO]⁻, 314.0 (13) [M-H-2x Ar²SO₂NH₂]⁻, 288 (4) [M-H—Ar²SO₂NCO—Ar²SO₂NH₂]⁻.

¹H NMR (500 MHz, ACN-d₃): δ(ppm)=8.92 (1H, s), 8.64 (1H, s), 8.06 (1H, s), 7.94 (1H, s), 7.88-7.82 (5H, m), 7.59 (1H, d, J=8.8 Hz), 7.38-7.31 (4H, m), 7.15 (1H, dd), 7.14-7.10 (2H, m), 7.02-6.98 (1H, m), 6.98-6.95 (2H, m), 2.39 (3H, s), 2.37 (3H, s)

¹³C NMR (126 MHz, ACN-d₃): δ(ppm)=149.76 (NH$\underline{C}$(O)NH), 149.61 (NH$\underline{C}$(O)NH), 146.07, 146.06, 143.80, 137.48, 137.34, 137.29, 137.04, 131.79, 130.66, 130.58, 130.21, 128.68, 128.60, 126.74, 123.08, 122.39, 114.66, 113.28, 21.68 ($\underline{C}$H₃), 21.65 ($\underline{C}$H₃).)

XXXIII, $C_{32}H_{28}N_6O_{10}S_4$, M=784.8, N¹,N³-diphenyl-4,6-bis(3-(phenyl sulfonyl)ureide)benzene-1,3-disulfonamide MS (ESI): m/z (%)=783.1 (100) [M-H]⁻, 626.0 (75) [M-H—Ar²SO₂NH₂]⁻, 600.0 (5) [M-H—Ar²SO₂NCO]⁻, 469.0 (50) [M-H-2x Ar²SO₂NH₂]⁻, 442.9 (8) [M-H—Ar²SO₂NCO—Ar²SO₂NH₂]⁻.

¹H NMR (500 MHz, DMSO-d₆): δ(ppm)=11.93 (2H, s), 10.45 (2H, s), 8.71 (2H, s), 8.48 (1H, s), 8.15 (1H, s), 7.88-7.84 (4H, m), 7.77-7.71 (2H, m), 7.61-7.55 (4H, m), 7.13-7.07 (4H, m), 7.00-6.92 (6H, m).

¹³C NMR (126 MHz, DMSO-d₆): δ(ppm)=148.46 (NH$\underline{C}$(O)NH), 139.76, 139.36, 135.87, 133.58, 129.17, 129.12, 128.84, 127.41, 125.54, 121.12, 120.98, 119.09.

XXXIV, $C_{34}H_{32}N_6O_{10}S_4$, M=812.9, N¹,N³-diphenyl-4,6-bis(3-tosylureide)benzene-1,3-disulfonamide MS (ESI): m/z (%)=811.0 (100) [M-H]⁻, 640.0 (70) [M-H—Ar²SO₂NH₂]⁻, 614.1 (8) [M-H—Ar²SO₂NCO]⁻.

¹H NMR (500 MHz, DMSO-d₆): δ(ppm)=11.85 (2H, s), 10.44 (2H, s), 8.70 (2H, s), 8.52 (1H, s), 8.15 (1H, s), 7.88-7.83 (4H, m), 7.48-7.42 (4H, m), 7.13-7.07 (4H, m), 6.99-6.93 (6H, m), 2.43 (6H, s), $^{13}$C NMR (126 MHz, DMSO-d$_6$): δ(ppm)=148.44 (NH$\underline{C}$(O)NH), 144.14, 139.81, 136.51, 135.88, 129.54, 129.2$\overline{2}$, 129.17, 127.49, 125.58, 121.01, 120.92, 119.08, 21.04 ($\underline{C}$H$_3$).

XXXV, C$_{40}$H$_{40}$N$_6$O$_{14}$S$_4$, M=957.03, diethyl 4-4'-((4,6-bis(3-tosylureide tosylureide)-1,3-phenylene disulfonyl)bis(azanediyl))dibenzoate MS (ESI): m/z (%)=955.1 (55) [M-H]$^-$, 784.1 (100) [M-H—Ar$^2$SO$_2$NH$_2$]$^-$, 758.1 (7) [M-H—Ar$^2$SO$_2$NCO]$^-$, 613.0 (40) [M-H-2x Ar$^2$SO$_2$NH$_2$]$^-$, 587.0 (8) ([M-H—Ar$^2$SO$_2$NCO—Ar$^2$SO$_2$NH$_2$]$^-$.

$^1$H NMR (500 MHz, DMSO-d$_6$): δ(ppm)=11.80 (2H, s), 11.06 (2H, s), 8.77 (2H, s), 8.52 (1H, s), 8.28 (1H, s), 7.89-7.81 (4H, m), 7.71-7.65 (4H, m), 7.44-7.39 (4H, m), 7.04-6.98 (4H, m), 4.28 (4H, q, J=7.0 Hz), 2.42 (6H, s), 1.30 (6H, t, J=7.0 Hz).

$^{13}$C NMR (126 MHz, DMSO-d$_6$): δ(ppm)=164.78 ($\underline{C}$O$_2$R), 148.51 (NH$\underline{C}$(O)NH), 144.16, 140.61, 139.98, 136.43, 130.43, 129.55, 129.21, 127.50, 125.59, 125.53, 121.13, 118.44, 60.52 (O$\underline{C}$H$_2$CH$_3$), 21.01 ($\underline{C}$H$_3$), 14.04 (OCH$_2\underline{C}$H$_3$).

An aqueous application suspension to form the heat-sensitive color-forming layer of a heat-sensitive recording paper was applied in the laboratory standard using a rode blade to one side of a synthetic base paper (Yupo® FP680) of 63 g/m². After drying, a thermic recording sheet was obtained. The application quantity of the heat-sensitive color-forming layer was between 4.0 and 4.5 g/m².

The application of the aqueous application suspension in the production standard to a roll of paper with a base weight of 43 g/m² using the curtain-coating method. The viscosity of the aqueous application layer was 450 mPas (according to Brookfield, 100 rpm, 20° C.) (deaerated). Its surface tension was 46 mN/m (statistic ring method). The coating apparatus was arranged inline. The curtain coating method was operated at a speed of 1550 m/min.

After applying the aqueous application suspension, the drying process of the layered paper backing took place in the usual way. The base weight application of the dried heat-sensitive layer was 4.0-4.5 g/m².

Based on the previously stated specifications, a heat-sensitive recording material or thermal paper was produced, wherein the following recipes of aqueous application suspensions were used to form a compound structure on a supporting substrate and then the further layers, in particular a protective layer, were formed in the typical way, about which greater details need not be provided here.

Production of the dispersions (each for 1 weight percent) for the application suspensions.

The aqueous Dispersion A (color former dispersion) is produced by grinding 20 weight percent of 3-N-n-dibutylamine-6-methyl-7-anilinofluoran (ODB-2) with 33 weight percent of a 15% aqueous solution of Ghosenex™ L-3266 (sulfonated polyvinyl alcohol, Nippon Ghosei) in a pearl mill.

The aqueous Dispersion B (color developer dispersion) is produced by grinding 40 weight percent of the color developer together with 66 weight percent of a 15% aqueous solution of Ghosenex™ L-3266 in the pearl mill.

The aqueous Dispersion C (sensitizer dispersion) is produced by grinding 40 weight percent of sensitizers with 33 weight percent of a 15% aqueous solution of Ghosenex™ L-3266 in a pearl mill.

The aqueous Dispersion D (anti-aging agent or stabilizer dispersion) is produced by grinding 12.5 weight percent UU (urea-urethane) with 10 weight percent of a 15% aqueous solution of Ghosenex™ L-3266 in a pearl mill.

All dispersions obtained by grinding have an average grain size D$_{(4,3)}$ of 0.80-1.20 µm.

The Dispersion E (lubricant dispersion) is a 20% zinc stearate dispersion consisting of 9 weight percent Zn-stearate, 1 weight percent Ghosenex™ L-3266 and 40 parts water.

Pigment P is a 72% coating kaolin suspension (Lustra® S, BASF).

The Binder consists of a 10% aqueous polyvinyl alcohol solution (Mowiol 28-99, Kuraray Europe).

The application suspension is produced by mixing the dispersions while stirring according to the quantity specifications in Table 3 taking into consideration the order B, E, C, D, P, A, Binder and brought with water to a solid content of approx. 25%.

The measurement of the grain size distribution of the application dispersions took place using laser diffraction with a Coulter LS230 device from Beckman Coulter.

TABLE 3

Summary of the recipes for the application dispersions (weight percent)

| Components | Recipe | |
|---|---|---|
| | R1 | R2 |
| A | 1 | 1 |
| B | 1 | 1 |
| C | 1 | 1 |
| D | 0 | 1 |
| E | 56 | 56 |
| P | 146 | 126 |
| Binder | 138 | 138 |

The heat-sensitive layering suspensions thus obtained were used to produce compound structures of paper backing and thermoreactive layers.

The thermic recording materials according to Table 3 were evaluated as described below.

(1) The paper whiteness on the coating side was determined according to DIN/ISO 2470 with an Elrepho 3000 spectral photometer (uncertainty of whiteness value measurements ≤50.5%).

(2) Dynamic color thickness:

The papers (6-cm wide strips) were thermally printed upon using the Atlantek 200 test printer (Atlantek, USA) with a 200-dpi, 560-Ohm Kyocera pressure bar with an applied voltage of 20.6 V and a maximum pulse width of 0.8 ms with a chessboard pattern with 10 energy phases. The image thickness (optical thickness, opt. thickness) was measured with a Macbeth densitometer RD-914, from Gretag, wherein the value "½" corresponds to the the o.t. with an energy level of 0.4 ms and the value "max." corresponds to the energy level of 0.8 ms. The uncertainty of the o.t. value measurements was estimated at ±0.02 optical thickness units.

(3) Statistic color thickness (start temperature):

The recording sheet is pressed against a row of temperature-regulated metallic stamps heated to different temperatures with a pressure of 0.2 kg/cm² and a contact time of 5 sec (thermal tester TP 3000QM, Maschinenfabrik Hans Rychiger AG, Steffisburg, Switzerland). The image thickness (opt. thickness) of the images produced in this way is measured with a Macbeth densitometer RD-914 from Gretag. The static starting point is by definition the lowest temperature at which an optical thickness of 0.2 is achieved. The precision of the measurement method is ≤±0.5° C.).

(4) Durability test of the printed image:

(4.1) Plasticizer durability:

A plasticizer-containing plastic wrap (PVC wrap with 20-25% dioctyl adipate) was brought into contact with the thermic recording paper sample dynamically recorded according to the method of (2), avoiding folding and air bubbles, wrapped into a roll and stored for 16 hours. A sample is stored at room temperature (20-22° C.), a second at 40° C. After removing the plastic, the image thickness (opt. thickness) was measured and related to the corresponding image thickness values before the plasticizer action according to the formula (IV).

(4.2) Durability vis-à-vis adhesive:

A strip of Tesa transparent self-adhesive tape (Tesafilm® crystal-clear, #57315) and separately a strip of Tesa packaging tape (#04204) were each adhered to the thermic recording paper sample dynamically recorded according to the method of (2), avoiding folding and air bubbles. After 24-hour storage at room temperature (20-22° C.), the image thickness (opt. thickness) was measured—through the respective tape—and related to the analogously determined image thickness values of the freshly adhered pattern according to the formula (IV). The value thus obtained corresponds to the % decrease in the original image intensity.

$$\% \text{ change in the o.t.} = \left(\frac{\text{image thickness after test}}{\text{image thickness before test}} - 1\right) * 100 \quad (IV)$$

The mean variation in the % values calculated according to (IV) are ±2 percent points.

LC-MS: Device type HPLC: Agilent 1200 series, column: Synergi 4µ Fusion-RP80A (250×4.6 mm, Phenomenex Inc.).

Eluent A: acetonitrile/water±0.1% formic acid (60/40, v/v).

Eluent B: acetonitrile+0.1% formic acid.

Gradient: 0.0 min 100% A→8.0 min 100% A (0.4 ml/min)→10.0 min 100% A (1.0 ml/min)→11 min 20% A (1.0 ml/min)→20.0 min 20% A (1.0 ml/min)→22.0 min 100% A (0.4 ml/min).

DAD Detector G1315C (Agilent), scanned wavelength range 200-400 nm.

Single Quadrupole Mass Spectrometer, Type 6120B (Agilent) with electrospray ionization (ESI), positive and negative ion mode, scanned mass range 100-1000 m/z.

Table 4 summarizes the evaluation of the manufactured recording materials.

Table 5 presents, for chosen developer substances of the compound class according to the invention, possibilities, by way of example, to improve the image stability with anti-aging agents without hindering other performance properties.

TABLE 4

Evaluation of the paper pattern with recipe R1

| | | Background whiteness (%) | | | | Durability of the printed image | | | |
|---|---|---|---|---|---|---|---|---|---|
| | | | | Opt. thickness | | Static starting point | TESA, 24 h, (at max. o.t.) | | Plasticizer foil, 16 h, (at max. o.t.) |
| | | 1 day | 7 day | | | | | | |
| No. | Developer | R.T. | R.T. | ½ | Max. | (° C.) | #57315 | #04204 | RT | 40° |
| 1 | I | 87 | 87 | 1.36 | 1.35 | 80.5 | −43 | −70 | −7 | −40 |
| 2 | III | 89 | 89 | 1.26 | 1.32 | 85.5 | −38 | −67 | −9 | −76 |
| 3 | IV | 89 | 88 | 1.25 | 1.27 | 81.5 | −37 | −66 | −6 | −34 |
| 4 | VII | 86 | 86 | 1.28 | 1.31 | 76.5 | −36 | −60 | −5 | −27 |
| 5 | X | 89 | 90 | 1.25 | 1.27 | 85.0 | −45 | −70 | −9 | −63 |
| 6 | XII | 89 | 89 | 1.27 | 1.29 | 81.0 | −37 | −60 | −6 | −40 |
| 7 | XV | 89 | 89 | 1.30 | 1.30 | 81.5 | −25 | −48 | −5 | −20 |
| 8 | XVIII | 88 | 88 | 1.32 | 1.31 | 78.0 | −37 | −57 | −8 | −42 |
| 9 | XXIII | 89 | 89 | 1.25 | 1.29 | 81.5 | −26 | −50 | −5 | −26 |
| 10 | XXXII | 87 | 87 | 1.15 | 1.20 | 80.0 | −14 | −13 | −4 | −10 |
| 11 | XXXV | 87 | 87 | 1.23 | 1.26 | 82.5 | −6 | −5 | −2 | −9 |
| 12 | FE A* | 88 | 88 | 1.26 | 1.29 | 76.5 | −32 | −57 | −5 | −31 |
| 13 | FE B* | 89 | 89 | 1.25 | 1.28 | 85.5 | −50 | −70 | −15 | −91 |

*non-phenolic developers of the prior art

TABLE 5

Evaluation of the paper pattern without/with anti-aging agents (AAA) with recipe R2

| | | Background whiteness (%) | | | | Durability of the printed image | | | |
|---|---|---|---|---|---|---|---|---|---|
| | | | | Opt. thickness | | Static starting point | TESA, 24 h, (at max. o.t.) | | Plasticizer foil, 16 h, (at max. o.t.) |
| | | 1 day | 7 day | | | | | | |
| No. | Developer | R.T. | R.T. | ½ | Max. | (° C.) | #57315 | #04204 | RT | 40° |
| 14 | II | 89 | 89 | 1.21 | 1.28 | 86 | −44 | −75 | −15 | −67 |
| 15 | II/AS | 90 | 88 | 1.21 | 1.21 | 83 | −32 | −59 | −4 | −18 |

TABLE 5-continued

Evaluation of the paper pattern without/with anti-aging agents (AAA) with recipe R2

| | | Background | | | | Durability of the printed image | | | |
|---|---|---|---|---|---|---|---|---|---|
| | | whiteness (%) | | | Static | TESA, 24 h, (at max. o.t.) | | Plasticizer foil, 16 h, (at max. o.t.) | |
| | | 1 day | 7 day | Opt. thickness | starting point | | | | |
| No. | Developer | R.T. | R.T. | ½ | Max. | (° C.) | #57315 | #04204 | RT | 40° |
| 16 | IX | 89 | 89 | 1.25 | 1.21 | 81 | −53 | −78 | −6 | −47 |
| 17 | IX/AS | 82 | 87 | 1.21 | 1.22 | 80 | −29 | −54 | −2 | −20 |
| 18 | XIV | 90 | 90 | 0.54 | 0.55 | 81 | −49 | −69 | −85 | −87 |
| 19 | XIV/AS | 88 | 90 | 0.84 | 0.95 | 78 | −43 | −45 | −13 | −40 |
| 20 | XXVI | 78 | 78 | 1.20 | 1.31 | 81 | −18 | −41 | −4 | −19 |
| 21 | XXVI/AS | 87 | 82 | 1.24 | 1.24 | 81 | −16 | −37 | −3 | −9 |

The heat-sensitive recording material of the present invention exhibits in particular the following advantageous properties:

(1) The surface whiteness of the heat-sensitive recording papers according to the invention is better than or comparable to the reference sample with color developers of the prior art both when fresh and after storage.

(2) The recorded image of the heat-sensitive papers according to the invention with the color developers according to the invention have a print thickness (optical thickness values "½" and "max"), which is in no way inferior to the color developers of the reference sample.

(3) The temperature starting at which a visually noticeable graying of the heat-sensitive recording materials according to the invention appears (static starting point) is comparable to or higher than in known heat-sensitive recording materials and meets the requirements for marketable heat-sensitive recording materials. A higher starting point is necessary for labeling applications in the field of groceries/medicine (thermic laminability, microwave and sterilizer suitability).

(4) The printed image (max. opt. thickness values from Table 4) is hardly faded after the action of hydrophobic agents (adhesives, plasticizers). The image durability is better than or comparable to when using known non-phenolic color developers.

(5) With typical anti-aging agents, if necessary, the image durability vis-à-vis hydrophobic agents of the papers according to the invention may be increased without disadvantages with regards to poor surface whiteness or low starting temperature (Table 5).

(6) With the production method according to the invention, a heat-sensitive recording material of top quality in all important application-specific regards may be produced in economically advantageous conditions.

The invention claimed is:

1. Heat-sensitive recording material comprising a supporting substrate as well as a heat-sensitive color-forming layer containing at least one color former and at least one phenol-free color developer, wherein the at least one color developer is the compound of the formula (I)

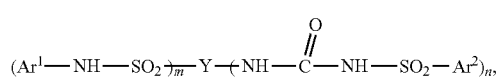   (I)

wherein m and n independently of one another are ≥1, $Ar^1$ is an unsubstituted phenyl radical or a monosubstituted phenyl radical substituted with a C1-05-alkyl radical, an alkenyl radical, an alkinyl radical, a benzyl radical, an RO radical, a halogen radical, an ROC radical, an RO2C radical, a CN radical, an NO2 radical, an R—SO2O radical, an RO—SO2 radical, an R—NH—SO2 radical, an R—SO2NH radical, an R—NH—CO—NH radical, an R—SO2-NH—CO—NH radical, an R—NH—CO—NH—SO2 radical or an R—CO—NH radical, wherein R is a C1-05-alkyl radical, an alkenyl radical, an alkinyl radical, a phenyl radical, a tolyl radical or a benzyl radical, $Ar^2$ is an unsubstituted phenyl radical or a monosubstituted phenyl radical or a phenyl radical substituted with a C1-C4 alkyl radical, and Y is at least one (m+n)-times substituted benzene or naphthalene group, wherein (m+n) is 2, 3 or 4 and wherein the compound of formula (1) is selected from N-phenyl-2-(3-(phenylsulfonyl)ureide)benzene sulfonamide; N-(4-tolyl)-2-(3-(phenylsulfonyl)ureide)benzene sulfonamide; N-(4-methoxyphenyl)-2-(3-(phenylsulfonyl)ureide)benzene sulfonamide; methyl 4-(2-(3-(phenylsulfonyl)ureide)phenyl sulfonamide) benzoate; N-(3-chlorophenyl)-2-(3-(phenylsulfonyl)ureide) benzene sulfonamide; 2-(3-(phenylsulfonyl)ureide)-N-(2-(3-phenylureido)phenyl)benzene sulfonamide; N-(2-tolyl)-2-(3-tosylureide)benzene sulfonamide; N-(4-tolyl)-2-(3-tosylureide)benzene sulfonamide; N-(3-tolyl)-2-(3-tosylureide)benzene sulfonamide; N-(4-methoxy-phenyl)-2-(3-tosylureide)benzene sulfonamide; methyl 4-(2-(3-tosylureide)phenyl sulfonamide) benzoate; N-(3-chlorphenyl)-2-(3-tosylureide)benzene sulfonamide; N-(4-chlorphenyl)-2-(3-tosylureide)benzene sulfonamide; 3-(2-(3-tosylureide)phenyl sulfonamide)phenyl 4-methyl benzene sulfonate; 4-methyl-N-((4-(N-(2-(3-phenylureide) phenyl) sulfamoyl)phenyl)carbamoyl)benzene sulfonamide; ethyl 4-(2-(3-tosylureide)phenyl) sulfonamide)benzoate; N-(2-(3-phenylureide)phenyl)-3-(3-tosylureide)benzene sulfonamide; N-phenyl-4-(3-tosylureide)benzene sulfonamide; N-(3-tolyl)-4-(3-tosylureide)benzene sulfonamide; methyl 4-(4-(3-tosylureide)phenyl sulfonamide)benzoate; N-(4-chlorphenyl)-4-(3-tosylureido)benzene sulfonamide; 4-methyl-N-((4-(N-(4-(3-phenylureide)phenyl)sulfamoyl) phenyl)carbamoyl)benzene sulfonamide; ethyl 4-(4-(3-tosylureide)phenyl sulfonamide)benzoate; N,N'-(((4-(N-phenyl sulfamoyl)-1,3-phenylene)bis(azanediyl))bis(carbonyl))bis (4-methyl benzene sulfonamide); $N^1,N^3$-diphenyl-4,6-bis(3-(phenyl sulfonyl)ureide)benzene-1,3-disulfonamide; $N^1,N^3$-diphenyl-4,6-bis(3-tosylureide)benzene-1,3-disulfonamide; diethyl 4-4'-((4,6-bis(3-tosylureide)-1,3-phenylene disulfonyl)bis(azanediyl))dibenzoate; and combinations thereof.

2. Heat-sensitive recording material according to claim 1, wherein the at least one color former is a triphenyl methane dye, a fluoran dye, an azaphthalide dye and/or a fluorene dye.

3. Heat-sensitive recording material according to claim 1, wherein in addition to the compound of the formula (I) one or more additional non-phenolic color developers are present.

4. Heat-sensitive recording material according to claim 1, wherein the compound of the formula (I) is present in a quantity of approximately 3 to approximately 35 weight percent, referring to the total solid content of the heat-sensitive layer.

5. Heat-sensitive recording material according to claim 1, wherein the heat-sensitive color-forming layer contains a urea-urethane compound of the general formula (II)

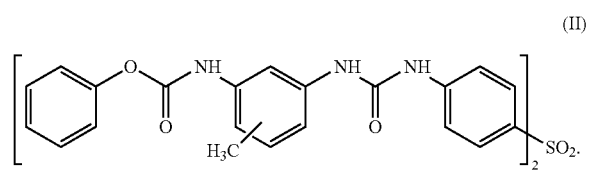

(II)

6. Heat-sensitive recording material according to claim 1, wherein that at least one color former is a fluoran.

7. Heat-sensitive recording material according to claim 1, wherein Y is substituted benzene, m=1 and n=1.

8. Method for producing a heat-sensitive recording material according to of claim 1, wherein on the supporting substrate is applied an aqueous suspension containing the at least one color former and the at least one phenol-free color developer of the heat-sensitive color-forming layer, wherein the aqueous suspension has a solid content of approximately 20 to approximately 75 weight percent, and is applied with the curtain-coating method at a coater operating speed of at least approximately 400 m/min, and then is dried.

9. Method of claim 8, wherein the aqueous suspension has a sold content of approximately 30 to approximately 50 weight percent and is applied with the curtain-coating method at a coater operating speed of at least approximately 1500 m/min.

10. Heat-sensitive recording material obtainable according to the method according to claim 8.

* * * * *